(12) United States Patent
Elbaz et al.

(10) Patent No.: US 10,500,164 B2
(45) Date of Patent: Dec. 10, 2019

(54) NANOPARTICLE-BASED COMBINATORIAL THERAPY

(71) Applicant: The American University in Cairo, New York, NY (US)

(72) Inventors: Nancy Mohamed Elbaz, Nasr (EG); Wael Mamdouh Sayed Sayed Ahmed, Cairo (EG); Laila Ziko, Cairo (EG); Rania Siam, Cairo (EG)

(73) Assignee: The American University in Cairo, New York, NY (US)

( * ) Notice: Subject to any disclaimer, the term of this patent is extended or adjusted under 35 U.S.C. 154(b) by 0 days.

(21) Appl. No.: 15/512,288

(22) PCT Filed: Sep. 18, 2015

(86) PCT No.: PCT/US2015/050926
§ 371 (c)(1),
(2) Date: Mar. 17, 2017

(87) PCT Pub. No.: WO2016/044716
PCT Pub. Date: Mar. 24, 2016

(65) Prior Publication Data
US 2017/0258736 A1    Sep. 14, 2017

Related U.S. Application Data

(60) Provisional application No. 62/052,841, filed on Sep. 19, 2014.

(51) Int. Cl.
*A61K 9/51* (2006.01)
*A61K 31/704* (2006.01)

(52) U.S. Cl.
CPC .......... *A61K 9/5115* (2013.01); *A61K 9/5138* (2013.01); *A61K 9/5146* (2013.01); *A61K 31/704* (2013.01)

(58) Field of Classification Search
None
See application file for complete search history.

(56) References Cited

U.S. PATENT DOCUMENTS

| | | | |
|---|---|---|---|
| 2007/0264199 A1 | 11/2007 | Labhasetwar | |
| 2011/0085987 A1 | 4/2011 | Wang | |
| 2011/0312877 A1* | 12/2011 | Berninger | A61K 39/07 514/3.3 |
| 2012/0207795 A1 | 8/2012 | Zink | |
| 2013/0115271 A1 | 5/2013 | Zamboni | |
| 2014/0212479 A1 | 7/2014 | Zeinelden | |

FOREIGN PATENT DOCUMENTS

| | | | |
|---|---|---|---|
| CN | 102885785 A * | 1/2013 | |
| CN | 102885785 | 1/2014 | |
| WO | WO-0217962 A2 * | 3/2002 | A61K 39/395 |

OTHER PUBLICATIONS

English language translation of CN 102885785 A. (Year: 2013).*

* cited by examiner

*Primary Examiner* — Craig D Ricci
*Assistant Examiner* — Dominic Lazaro
(74) *Attorney, Agent, or Firm* — Lumen Patent Firm

(57) ABSTRACT

The present invention provides a nano-particle based structure or composition for a combinational cancer therapy. The structure has a doxorubicin (DOX) physically loaded on core-shell silver polymeric nanoparticles (AgN-Ps) with a ratio of 3.3-5.5% doxorubicin to 1% silver to 2-10% polymer. This structure enhances the cellular uptake of DOX in comparison to the current conventional combination therapy. The DOX-loaded nano-particles result in an improved the therapeutic efficiency of DOX, and reduced its toxicity, which cannot occur in case of adding DOX and AgNPs.

3 Claims, 13 Drawing Sheets

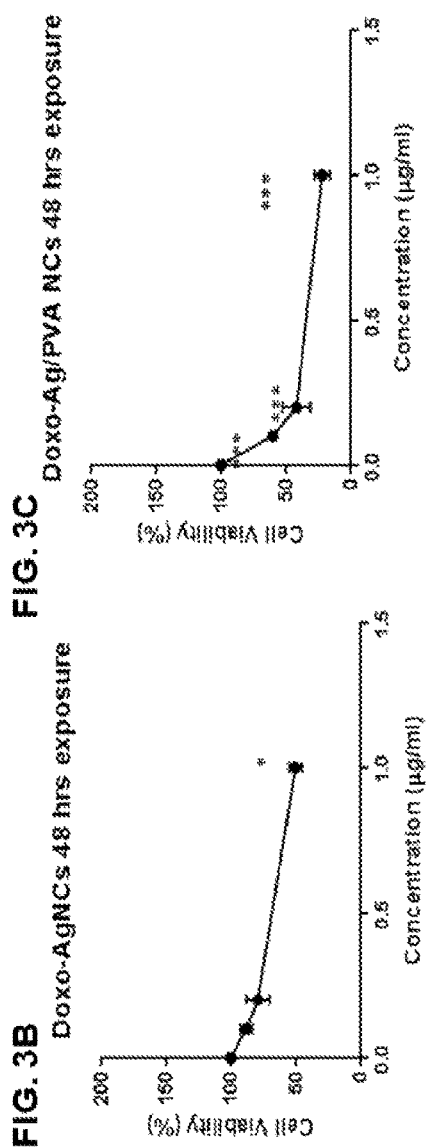
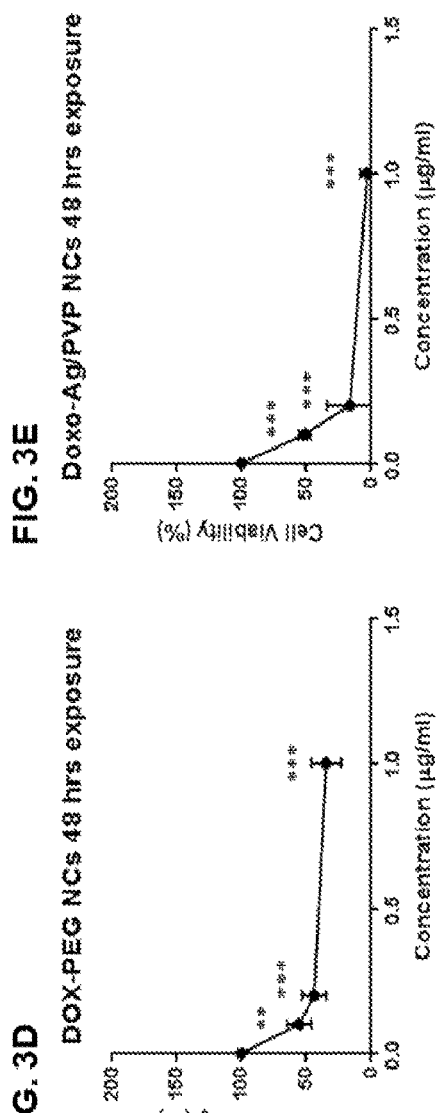
FIG. 3A  DOX 48 hrs exposure
FIG. 3B  Doxo-AgNCs 48 hrs exposure
FIG. 3C  Doxo-Ag/PVA NCs 48 hrs exposure
FIG. 3D  DOX-PEG NCs 48 hrs exposure
FIG. 3E  Doxo-Ag/PVP NCs 48 hrs exposure

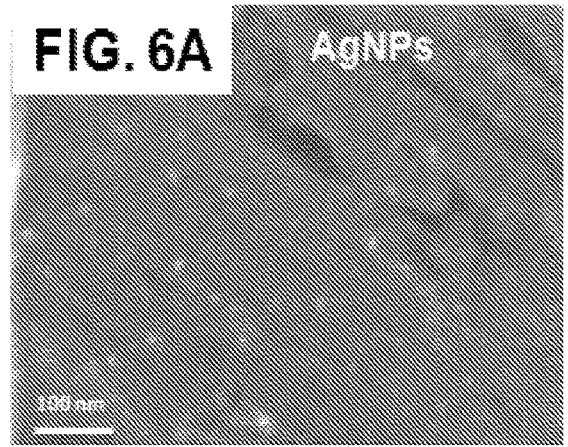
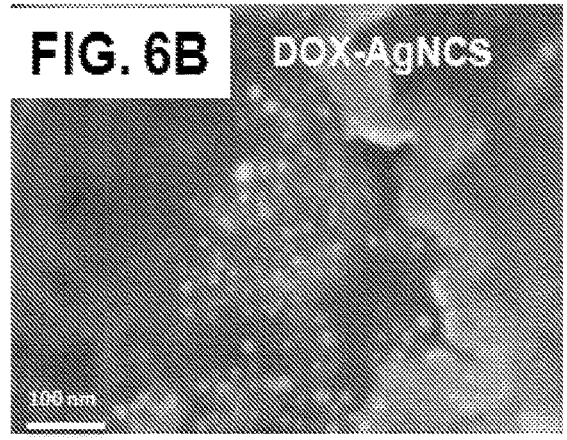
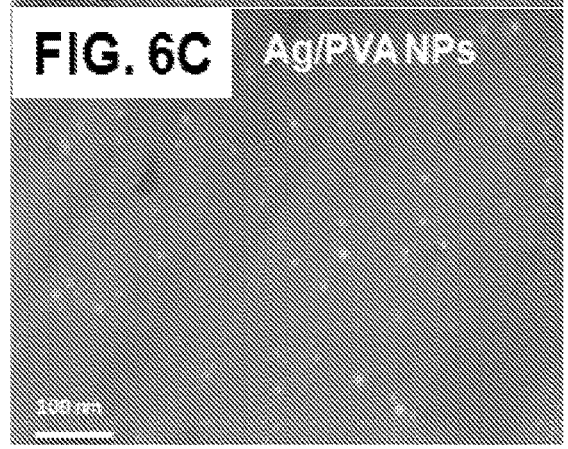
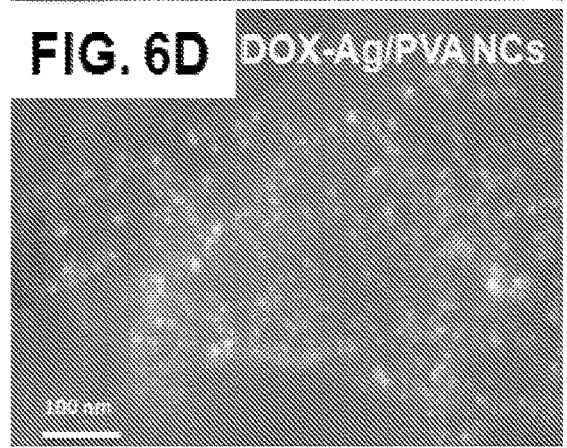
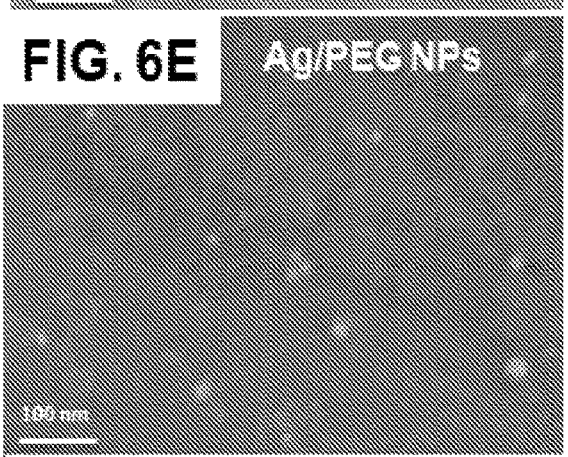
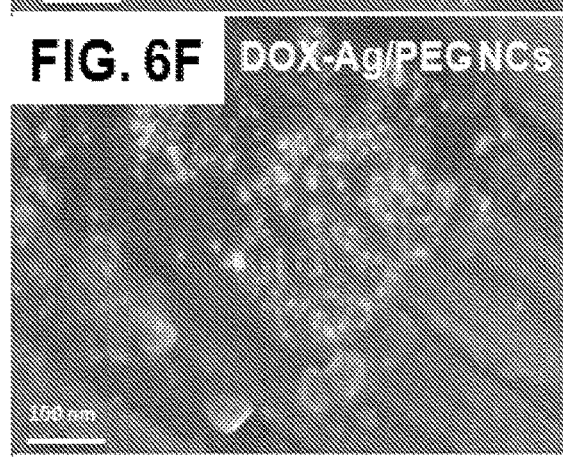
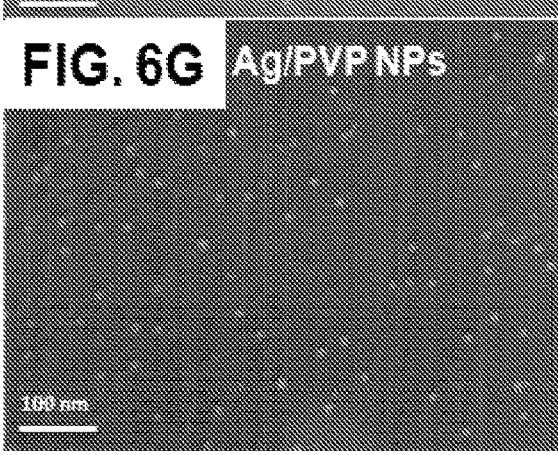
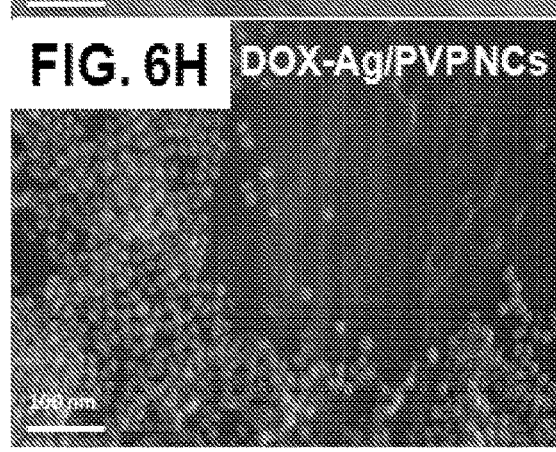

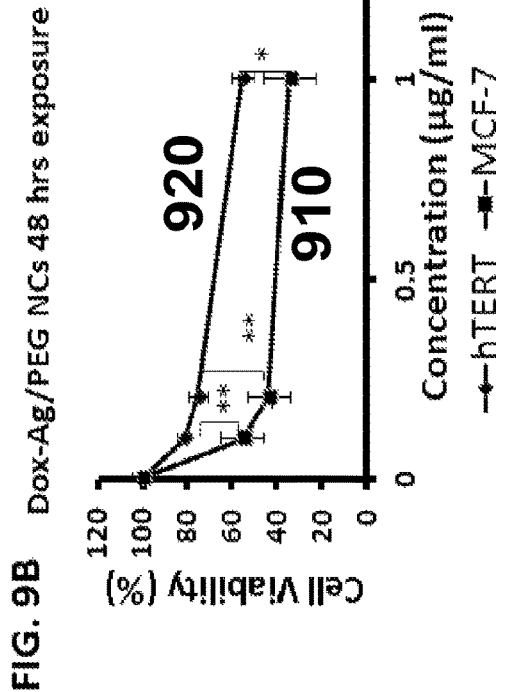
FIG. 9B  Dox-Ag/PEG NCs 48 hrs exposure
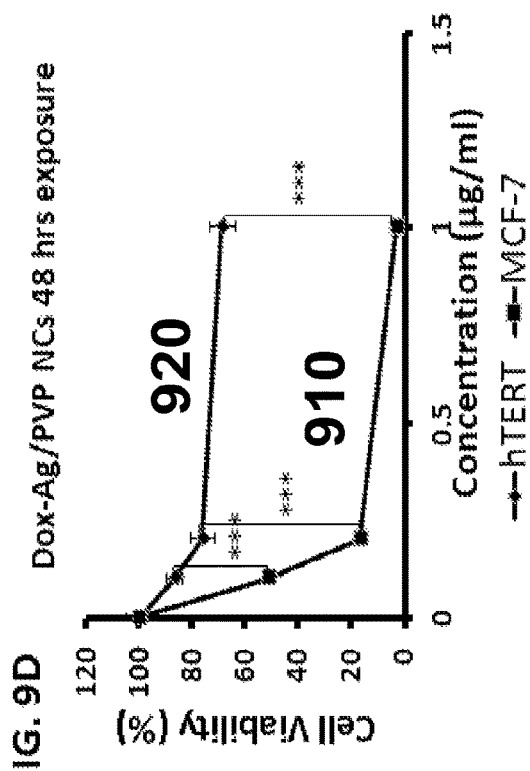
FIG. 9D  Dox-Ag/PVP NCs 48 hrs exposure
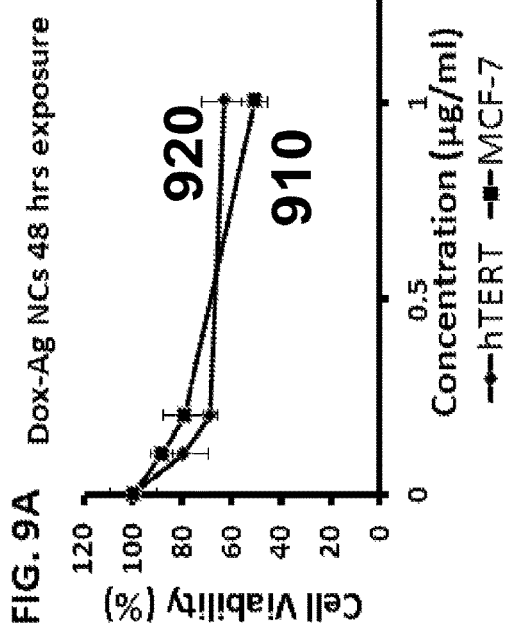
FIG. 9A  Dox-Ag NCs 48 hrs exposure
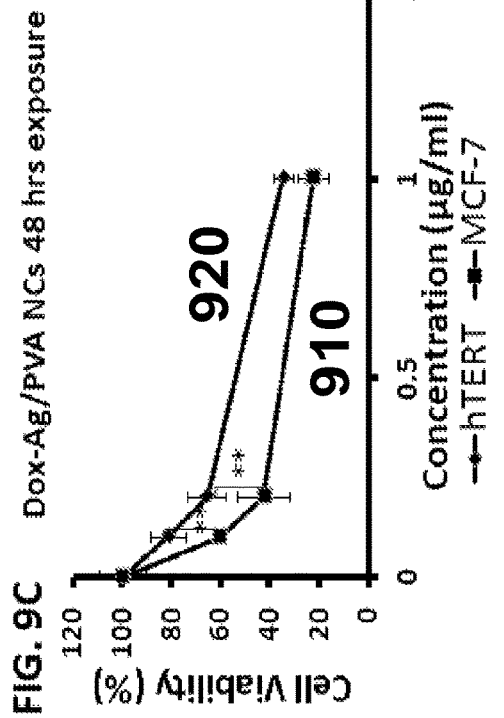
FIG. 9C  Dox-Ag/PVA NCs 48 hrs exposure

NANOPARTICLE-BASED COMBINATORIAL THERAPY

CROSS-REFERENCE TO RELATED APPLICATIONS

This application is a 371 of PCT application PCT/US2015/050926 filed on Sep. 18, 2015. PCT/US2015/050926 filed on Sep. 18, 2015 claims the benefit of U.S. Provisional application 62/052,841 filed on Sep. 19, 2014.

FIELD OF THE INVENTION

This invention relates to cancer treatments. In particular, the invention relates to nanoparticle-based combinatorial therapy for cancer treatments.

BACKGROUND OF THE INVENTION

Breast cancer is the most common type of cancer worldwide. Both men and women are susceptible to develop breast cancer, but the incidence of developing breast cancer is more common in women than in men. Worldwide, over 1.3 million women were diagnosed with breast cancer annually [1]. IARC reports a sharp increase in breast cancer incidence by 20% and mortality rate by 14% in 2012 compared with breast cancer incidence and mortality rate in 2008 [2]. Besides, the North American Association of Central Cancer Registries (NAACCR) reported that in 2013, breast cancer accounts for 29% of all new cancer cases in women and it is predicted to cause about 40,030 deaths in USA alone [3]. In Egypt, the National Cancer Institute (NCI) revealed that breast cancer is the most common cancer in women and accounts for 37.5% of all women cancers [4].

Chemotherapy either as a pre-operative therapy or a post-operative therapy is commonly used in the treatment of breast cancer. Basically, the main drawback of chemotherapeutics is their non-selective cytotoxic effect, which results in killing both cancer cells and normal cells, eventually causing severe adverse side effects such as bone marrow depression, neuropathy, nephropathy, GIT disorder, alopecia, etc. Doxorubicin (DOX) is the common chemotherapeutic agent used in clinic for the treatment of various cancers such as breast, lung and ovarian cancers. DOX, an anthracycline drug, possesses a potent anticancer action via inhibiting the topoisomerase-II-mediated DNA repair, intercalating with DNA, and causes DNA damage that eventually inducing cell apoptosis [5,6].

Despite its potent anticancer activity, DOX causes severe adverse side effects such as bone marrow depression, GI disorder, alopecia and cardiotoxicity. Cardiotoxicity is considered the main adverse side effect of DOX which limits its clinical use. DOX-medicated cardiotoxicity is dose-dependent since it was emphasized that the cumulative dose of DOX was the only confirmed risk factor for DOX-mediated cardiotoxicity. Beside the cardiotoxicity of doxorubicin, DOX has a short half-life, rapidly eliminated from the blood stream, resulting in low bioavailability of DOX at the tumor site. The low bioavailability of DOX provides only a partial treatment allowing some cancer cells to survive. These surviving cells mutate to prevent further DOX effect and being unresponsive to DOX; a phenomenon known as cancer resistance. Cancer resistance is a defense mechanism developed by cancer cells toward various chemotherapies such as DOX, and represents another obstacle limiting DOX clinical use. In fact, both resistance and systemic toxicity represent the main causes behind chemotherapy failure, which complicates cancer curability and leads to cancer progression [7-11].

Nanotechnology, a science of manipulating materials at the nano-scale, has received much attention across multiple disciplines as it offers novel and promising platforms suiting several industrial and biomedical applications. Nanotherapeutics is a targeted drug delivery system based on using nano-platforms (e.g. nanoparticles) as drug nano-carriers (NCs). These NCs such as NPs, have gained a great deal of attention in the biomedical field owing to their unique properties such as small sizes, large surface area, ease of surface modification, high stability and lower toxicity. All these unique NPs' properties offer a large drug loading capacity that permits drug loading to NPs via various strategies including drug encapsulation, physical drug loading over NPs' surfaces or covalent drug conjugation to NPs. Nanotherapeutics have provided desirable therapeutic characteristics over conventional therapy including prolonged systemic circulation lifetime, passive cancer targeting (selective killing of cancer cells) and nanoparticles-based combinatorial chemotherapy [12-14].

Nanotherapeutics provide a prolonged drug circulation half-life owing to the formulation of stealth NPs. Stealth NPs are considered a major breakthrough because of their ability to escape renal filtration, enzymatic degradation and the RES uptake and thus could circulate freely in the blood circulation [15, 12, 16]. Stealth NPs refer to NPs coated with polyethylene glycol (PEG), a synthetic hydrophilic polymer forming a hydration layer that sterically prevents biofouling, an accumulation of proteins and cells on the NPs surface, resulting in providing a prolonged drug systemic circulation half-life [13-14, 16-17]. Gabizon et al. conducted in-vivo studies to compare the pharmacokinetics between free doxorubicin and Doxil; DOX-loaded PEGylated-liposomes. It was found that the plasma concentration of Doxil was 300-fold higher than free doxorubicin in both human and animal studies. These studies confirmed that Doxil has an enhanced pharmacokinetics profile as compared to free doxorubicin [17]. Nanotherapeutics also provide a cancer targeted drug delivery system based on two mechanisms (i) passive targeting and (ii) active targeting. The passive targeting is based on NPs' small sizes and the enhanced permeability and retention (EPR) effect; a characteristic property of malignant tumors ascribed to their leaky blood vessels and poor lymphatic drainage. EPR effect is attributed to the improper angiogenesis developed by malignant tumor in order to obtain the required supplements to compensate its rapid proliferation. As a result, these leaky blood vessels are highly porous, allowing small and high molecular weight molecules such as NPs, which are a hundred times smaller than the red blood cells, to preferentially accumulate into the extracellular matrix of the tumor and become retained inside the cancer cells because tumor's vessels lack lymphatic drainage. Such a targeted drug delivery system increases the drug bioavailability at the tumor site and it also decreases the drug's adverse side effects. However, the conventional chemotherapy cannot take the advantage of EPR effect because the majority of chemotherapies have short half-lives. Consequently, these drugs are rapidly eliminated from the circulation by non-specific cellular and (RES) uptake as well as, enzymatic degradation before reaching the tumor site [5]. On the other hand, the active targeting mechanism depends on a discriminative property of cancer cells. Cancer cells exhibit an over-expression of specific receptors over their cell membranes that are not over-expressed by normal cells. Based on such a property, active targeting aimed at targeting these over-expressed receptors through employing a targeting or recognizing moiety such as antibodies or apatmers over the NCs' surfaces. This targeting moiety only recognizes and binds to its complementary receptor or protein, which is over-expressed over the surfaces of cancer cells. Such a targeting moiety delivers the anticancer agents to cancer cells specifically, leaving the neighboring normal cells untouched [16, 18]. Park et al. prepared Anti-human epidermal growth factor receptor2 (Anti-Her2)-conjugated liposomes and investigated their effects on HER-2 over-expressing breast cancer cells. It was reported that Anti-HER-2-conjugated liposomes demonstrated 700-fold higher cellular uptake compared to bare-liposomes [19]. Furthermore, the advent of nanotechnology permits the development of NPs-based combinatorial chemotherapy. These NPs-based combinatorial therapies enable co-delivery of multiple anticancer agents of different physiochemical properties using a single NC. Many clinically relevant reports stated that combinatorial chemotherapy became the main strategy to treat cancer particularly in the treatment of cancer chemo-resistance, as it promotes a synergistic anticancer action resulting in superior therapeutic efficacy when compared to single chemotherapy. Due to the aforementioned advantages, nanotherapeutics is considered an appealing approach for cancer therapy owing to its ability to improve chemotherapy's efficacy and pharmacokinetics profiles, which in turn results into minimizing the drug's dose and systemic toxicity.

SUMMARY OF THE INVENTION

The present invention provides a nanoparticles (NPs) based combinatorial cancer therapy composed of Ag nanoparticles loaded with anticancer agent. The NP-based combinatorial therapy relies on combining nanoparticles and has an anticancer effect along with an anticancer agent to achieve synergic cancer therapy that can selectively and effectively kill cancer cells with minimum toxicity The composition has a doxorubicin (DOX) physically loaded on core-shell silver polymeric nanoparticles (AgNPs) with a ratio of 3.3-5.5% doxorubicin to 1% silver to 2-10% polymer. Each nanoparticle has a width of 5 nm to 20 nm.

The core-shell silver-polymeric nanoparticle has a width of 20 nm to 40 nm. The concentration of the doxorubicin in the composition is less or equal to 0.2 µg/ml.

This composition enhances the cellular uptake of DOX in comparison to the current conventional combination therapy. The DOX-loaded nano-particles result in an improved the therapeutic efficiency of DOX, and reduced its toxicity, which cannot occur in case of adding DOX and AgNPs.

The silver polymeric nanoparticles are formed and stabilized by sodium citrate. This formation of AgNPs was confirmed by FT-IR spectroscopy (FIG. 10) The FT-IR spectra of AgNPs showed a band at 3423.6 cm$^{-1}$ that is not present in the FT-IR spectrum of AgNO$_3$. This band is attributed to O—H stretching between AgNPs and trisodium citrate. In addition, it was found that the band at 1592.8 cm$^{-1}$ is assigned for symmetric carboxylic group stretching mode of sodium citrate underwent a blue shift and appeared sharply at 1401 cm$^{-1}$ in the spectrum of AgNPs and thus confirming the stabilization of AgNPs by carboxylic group of trisodium citrate. Moreover, the spectrum of AgNO$_3$ displays a band at 1380 cm$^{-1}$ corresponding to ion pair Ag$^+$NO$_3^-$ that is not found in the spectrum of AgNPs due to the separation of NO$_3$ from its Ag$^+$ counterpart.

The core-shell silver polymeric nanoparticles have Ag as a core and Polyvinyl Alcohol (PVA), Polyethylene Glycol (PEG), or Polyvinyl Pyrrolidone (PVP) as a shell. The formation of core-shell Ag/PVA NPs (FIG. 11) was confirmed due to the presence of blue shift of band at 1424 cm$^{-1}$ in the spectrum of core-shell Ag/PVA NPs compared to the spectra of Ag nitrate, and PVA and thus indicating that PVA polymer is adsorbed on the surface of AgNPs via the interaction of AgNPs and OH groups of PVA. Moreover, the FT-IR spectrum of Ag/PEG NPs (FIG. 12) showed a broad band at 1099 cm$^{-1}$ as compared to FT-IR spectrum of PEG, which could be ascribed to C—O—H vibrations of AgNPs in PEG. Comparing the FT-IR of both pure PEG and core-shell Ag/PEG NPs, a strong band is observed at 509 cm$^{-1}$ at the spectrum of core-shell Ag/PEG NPs, which could be attributed to AgNPs banding with oxygen from hydroxyl groups of PEG chains and thus suggesting the existence of van der Waals interaction between the positively charged groups on the surface of Ag NPs and the negatively charged oxygen from the hydroxyl groups of PEG. Finally, the FT-IR spectrum of core-shell Ag/PVP NPs (FIG. 13) displays a red shift at band 1099 cm$^{-1}$, compared to the band at 1075 cm$^{-1}$ in the spectrum of pure PVP. The red shift of band at 1099 cm$^{-1}$ confirms the involvement of pyrrolidyl nitrogen electrons in the formation of core-shell Ag/PVP NPs. This emphasized that PVP is adsorbed at the silver NPs surfaces through donating electrons from the N atom to the Ag or the coordination between N and Ag.

In one exemplary result, DOX-core-shell Ag/polymeric (PVA, PEG, and PVP) NCs showed an anticancer effect on cancer (MCF-7) cells at much low dose, which is about 95% lower than free DOX and about 40% lower than the treatment in the prior art.

In another exemplary result, DOX-core-shell Ag/polymeric (PVA, PEG, and PVP) NCs showed a selective cytotoxicity toward cancer (MCF-7) cells than normal immortalized human fibroblast (1BR hTERT) cells. As shown in the MTT results (FIGS. 9B-C), the IC$_{50}$ of DOX-core-shell Ag/polymeric (PVA, PEG, and PVP) DOX-NCs (0.1-0.19 µg/ml DOX/3-3.5 µg/ml AgNPs) on cancer cells induce a low toxicity on normal cells.

In yet another exemplary result, DOX loading on AgNPs and core-shell Ag/polymeric (PVA, PEG, and PVP) NPs showed synergistic anticancer effect on MCF-7 cells due to the combined effect of Ag and DOX.

In still another exemplary result, core-shell AgNPs, Ag/PVA, Ag/PVP NPs showed a significant cytotoxicity on cancer cells, while mild toxicity on normal cells.

In still another exemplary result, among all the tested polymers used to coat the Ag, PVP-coated AgNPs exhibited the most significantly different percentage in the cytotoxic effect on MCF-7 breast cancer cells in comparison to 1BR hTERT cells at the concentration of 100 µg/ml (FIG. 8D).

In still another exemplary result, AgNPs coated with PEG were found not to kill MCF-7 cancer cells more than normal immortalized 1BR hTERT cells at all tested concentrations (FIG. 8C).

In still another exemplary result, AgNCs loaded with DOX did not kill MCF-7 cancer cells more than normal immortalized 1BR hTERT cells at all tested concentrations (FIG. 9A). Among all the loaded tested polymers used to coat the AgNCs, Dox-loaded PVP-coated NCs exhibited the most significantly different percentage in the cytotoxic effect on MCF-7 breast cancer cells in comparison to 1BR hTERT cells at the concentration of 0.1, 0.2 and 1 µg/ml (FIG. 9D).

In still another exemplary result, loading PEG-coated AgNCs with DOX rendered the NCs more cytotoxic against MCF-7 cells than normal immortalized 1BR hTERT cells at all tested concentrations (FIG. 9C).

In still another exemplary result, DOX-loaded PVA-Ag-NCs exhibited an increased cytotoxic effect on MCF-7 cells than normal immortalized 1BR hTERT cells only at concentrations of 0.1 and 0.2 μg/ml (FIG. 9B).

The invention can also be described as a method for treating a cancer in a subject (e.g. a human). A nanoparticle-based combinatorial therapy could be provided for delivery of an anticancer therapeutic agent (Doxorubicin) to cancer cells (e.g. breast cancer). A pharmaceutical composition is provided that has nanoparticles that have an anticancer effect. Each nanoparticle is formed by an Ag core and an FDA approved polymer shell. The purpose of the polymeric coating of the silver nanoparticles (AgNPs) is to increase its stability and prolong its circulation half-life in-vitro and in-vivo. The polymeric coating enhances the anticancer activity of AgNPs on cancer cells, while reducing its toxicity in-vitro.

The anticancer therapeutic agent is physically loaded into the core of AgNPs and core-shell Ag/polymeric nanoparticles, which administers the pharmaceutical composition to the cancer cells. The combination of AgNPs and the anticancer therapeutic agent possess a synergistic anticancer effect on cancer cells. The composition could be supplied parenteral, intravenous. The composition could be selectively targeted to a tumor site.

BRIEF DESCRIPTION OF THE DRAWINGS

FIGS. 3A-E show according to an exemplary embodiment of the invention cell viability percentage of MCF-7 cells after 48 hrs incubation with different concentrations of free DOX (FIG. 3A), DOX-AgNCs (FIG. 3B), DOX-Ag/PVA NCs (FIG. 3C), DOX-Ag/PEG NCs (FIG. 3D), and Ag/PVP NCs (FIG. 3E), respectively. All in-vitro results showed that cell viability decreased in a dose-dependent manner.

FIGS. 6A-H show according to an exemplary embodiment of the invention SEM images of NPs without DOX (FIGS. 6A, C, E and G) and DOX-Ag NCs and DOX-Ag/Polymeric NCs (FIGS. 6B, D, F and H), respectively.

FIGS. 8A-D show according to an exemplary embodiment of the invention the percentage of viable MCF-7 cells (810) and 1BR hTERT cells (820) as determined by the MTT assay following 48 hrs incubation with concentrations of 0, 10, 20, 50 and 100 μg/ml of: (FIG. 8A) AgNPs, (FIG. 8B) Ag/PVA NPs, (FIG. 8C) Ag/PEG NPs and (FIG. 8D) Ag/PVP NPs. The data are presented as a mean of at least three independent experiments (mean±SD). P values were calculated for each concentration between the two cell lines, and denoted if found to be significant (*$P<0.05$, $P<0.01$ and *$P<0.001$).

FIGS. 9A-D show according to an exemplary embodiment of the invention the percentage of viable MCF-7 cells (910) and 1BR hTERT cells (920) as determined by the MTT assay following 48 hrs incubation with concentrations of 0, 0.1, 0.2 and 1 μg/ml (concentrations are referring to DOX concentration) of: (FIG. 9A) DOX-Ag NCs, (FIG. 9B) DOX-Ag/PVA NCs (FIG. 9C) DOX-Ag/PEG NCs, and (FIG. 9D) DOX-Ag/PVP NCs. The data are presented as a mean of at least three independent experiments (mean±SD). P values were calculated for each concentration between the two cell lines, and denoted if found to be significant (*$P<0.05$, $P<0.01$ and *$P<0.001$).

DETAILED DESCRIPTION

The present invention entails the development of (NPs)-based combinatorial therapy composed of DOX-loaded on core-shell silver/polymeric (PVA, PEG, and PVP) NPs. This NPs-based combinatorial therapy is based on combining core-shell silver/polymeric (PVA, PEG, and PVP) nanoparticles, that it has an anticancer effect along with DOX aimed at achieving maximum therapeutic efficacy, while minimizing DOX's dose and systemic toxicity. The aim of this invention is to formulate a NPs-based combinatorial therapy that could (1) provide combination therapy possessing synergic anticancer action, (2) provide passive cancer targeting mechanism (which can selectively target and kill cancer cells without harming the neighboring normal cells), (3) improve pharmacokinetics profile of DOX, (4) improve therapeutic efficacy, (5) reduce DOX's dose, and (6) DOX's toxicity.

Method

Figure 1:
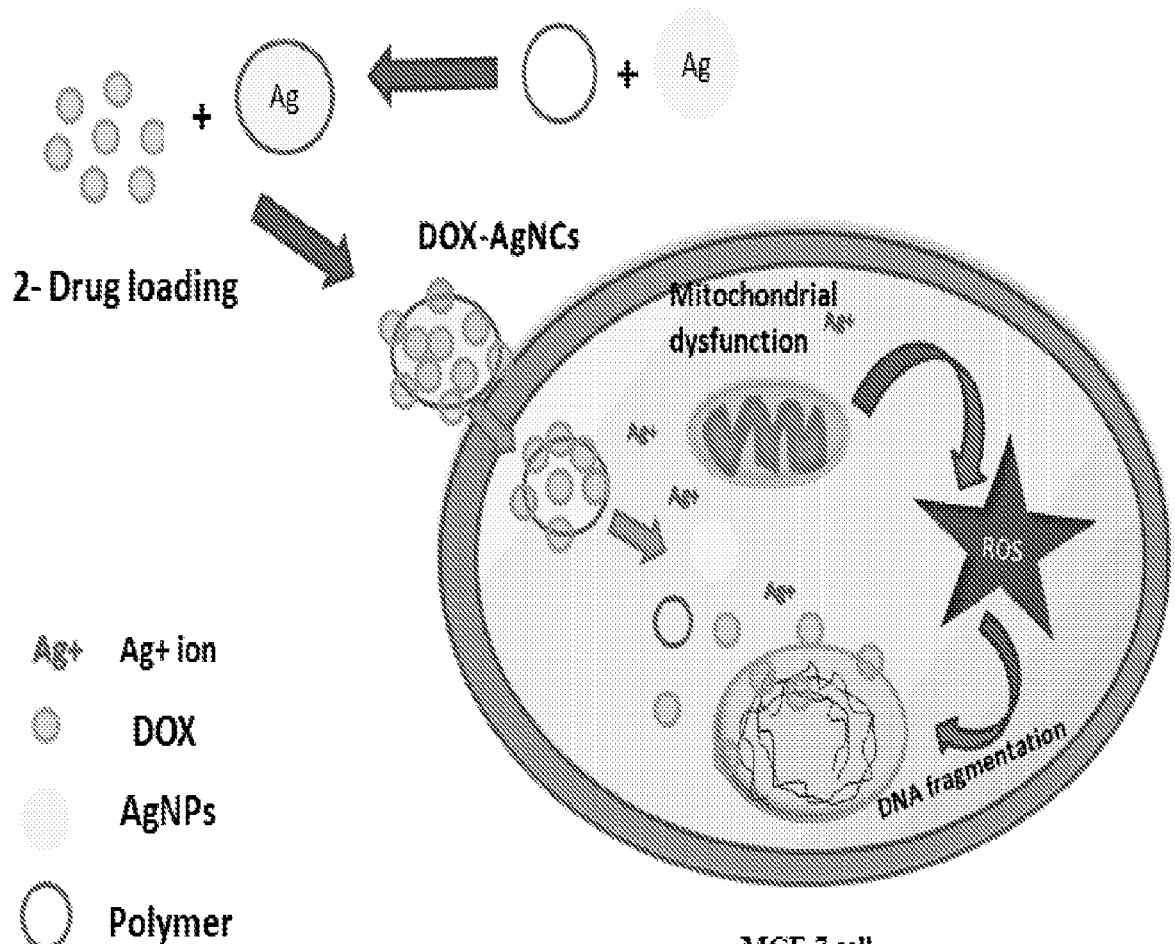
FIG. 1 shows according to an exemplary embodiment of the invention a schematic illustration of the NPs-based combination therapy. It further shows a study workflow and a mechanism of action behind the resultant synergic cytotoxic effect of DOX-loaded Ag/polymeric NCs at very low doses of DOX on MCF-7 cells. (Aspect 1) Preparation of NPs, (Aspect 2) DOX loading and (Aspect 3) $Ag^+$ ions and DOX intracellular release possibly leads to mitochondrial dysfunction that generates ROS leading to DNA fragmentation and cell death.
Figure 2A:
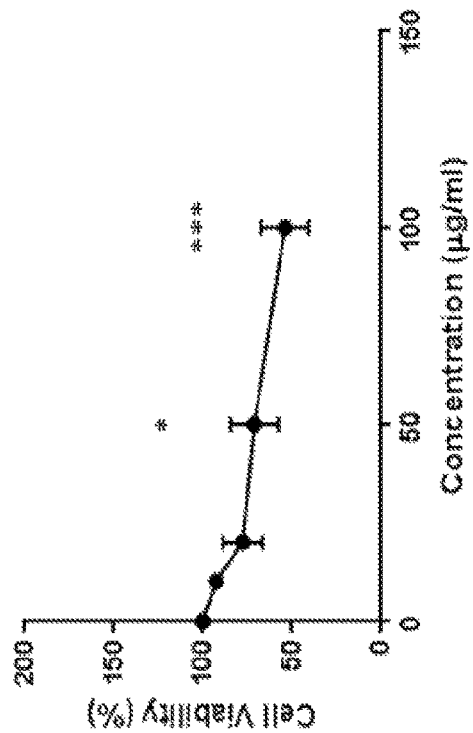
FIGS. 2A-D show according to an exemplary embodiment of the invention cell viability percentage of MCF-7 cells following 48 hrs incubation with different concentrations of Ag NPs (FIG. 2A), Ag/PVA NPs (FIG. 2B), Ag/PEG NPs (FIG. 2C) and Ag/PVP NPs (FIG. 2D), respectively. All in-vitro results showed that cell viability decreased in a dose-dependent manner.
Figure 2B:
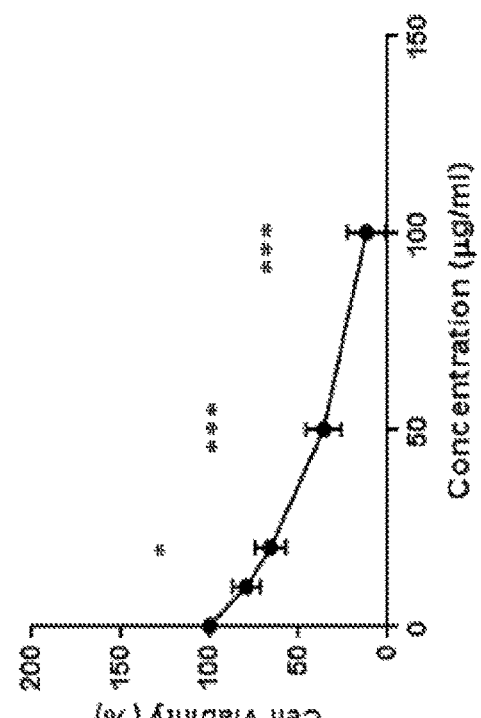
Figure 2C:
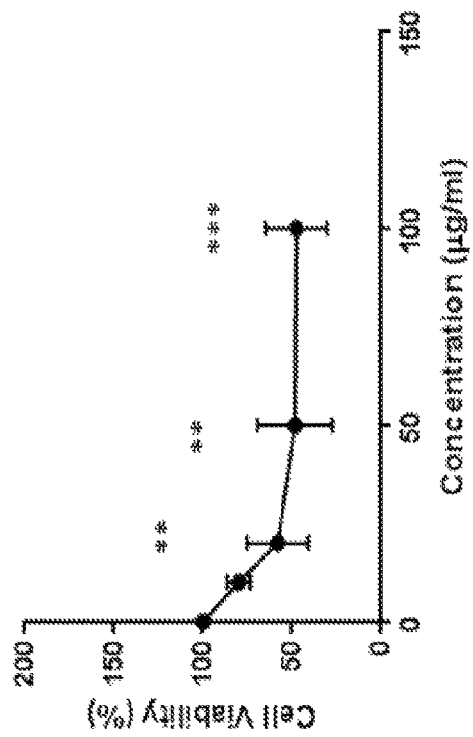
Figure 2D:
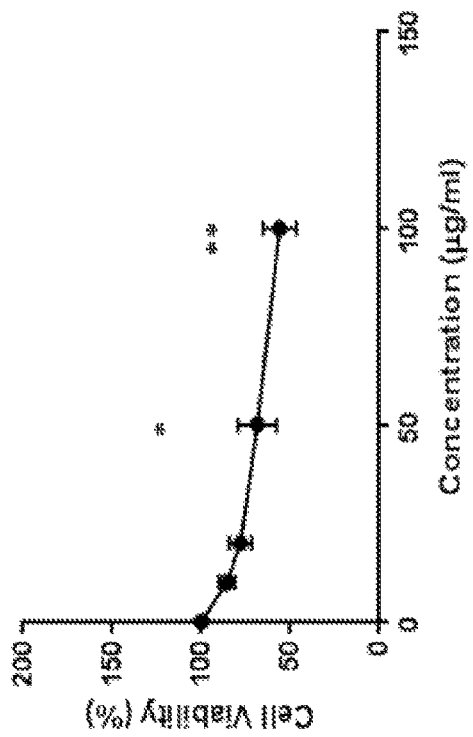
Figure 4A:
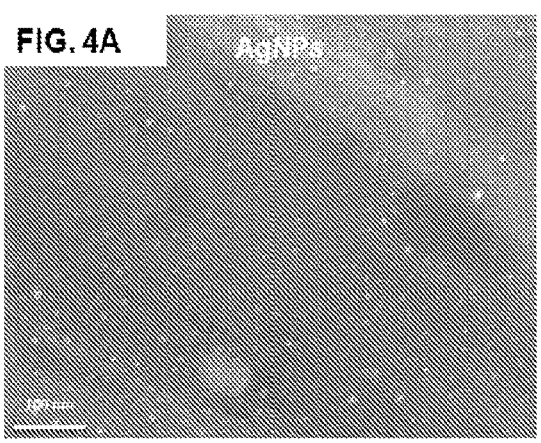
FIGS. 4A-H show according to an exemplary embodiment of the invention in FIGS. 4A, C, E and G representative SEM images of AgNPs, and core-shell Ag/polymeric NPs and in FIGS. 4B, D, F and H size and frequency histograms of AgNPs and core-shell Ag/polymeric NPs.
Figure 4B:
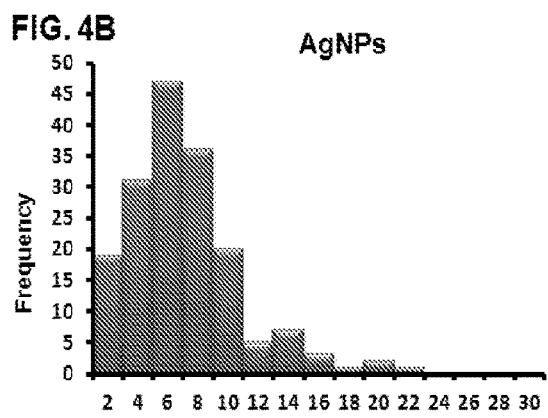
Figure 4C:
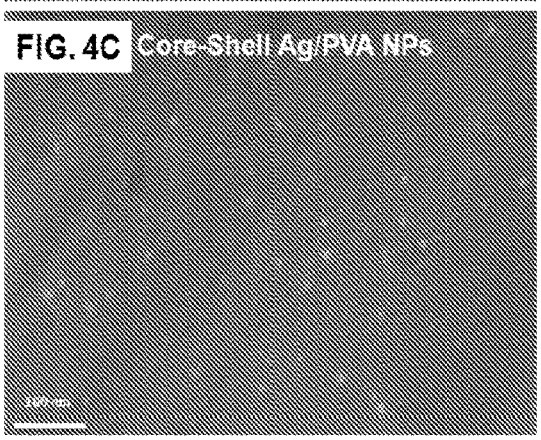
Figure 4D:
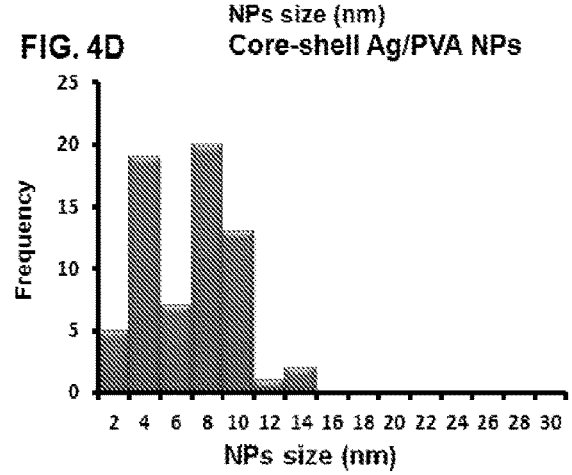
Figure 4E:
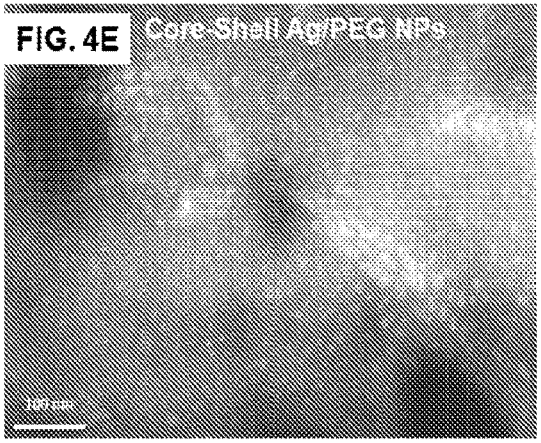
Figure 4F:
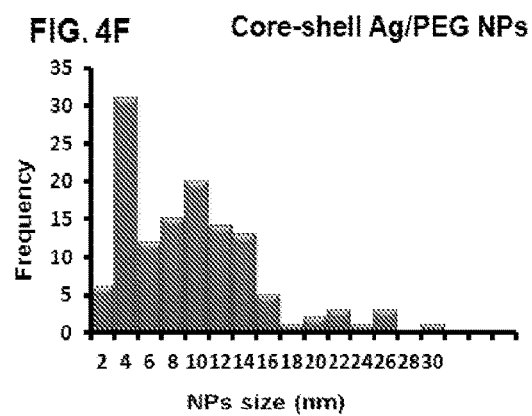
Figure 4G:
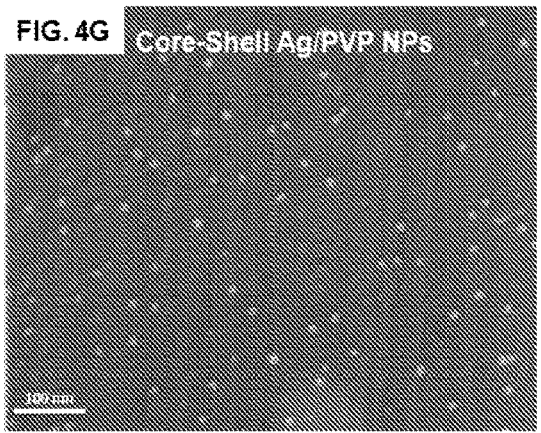
Figure 4H:
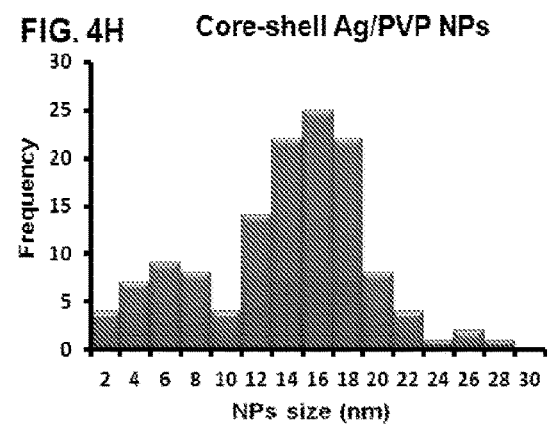
Figure 5A:
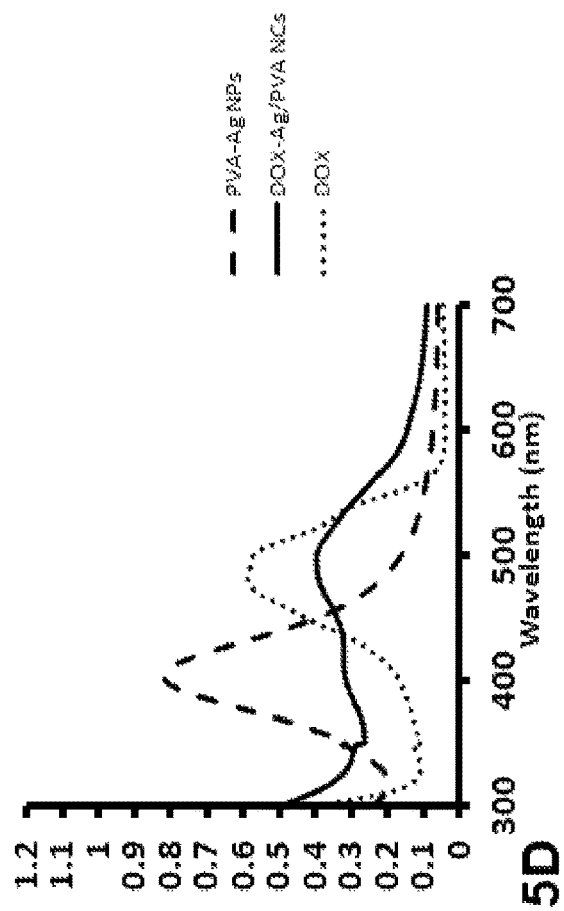
FIGS. 5A-D show according to an exemplary embodiment of the invention UV-Vis spectra of: DOX-AgNCs (FIG. 5A) and DOX-core-shell Ag/Polymeric (PVA, PEG, and PVP) NCs (FIG. 5B, FIG. 5C, and FIG. 5D). Each UV-Vis spectrum showed a comparison between UV-Vis spectra of NPs, DOX and DOX-NCs
Figure 5B:
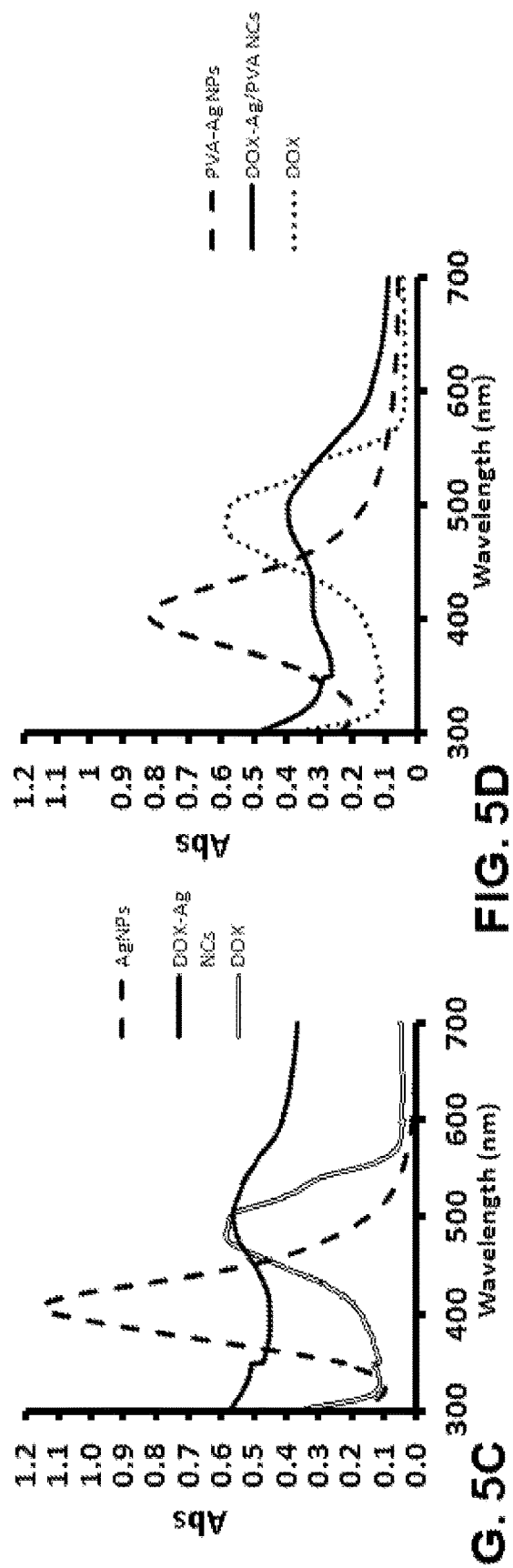
Figure 5C:
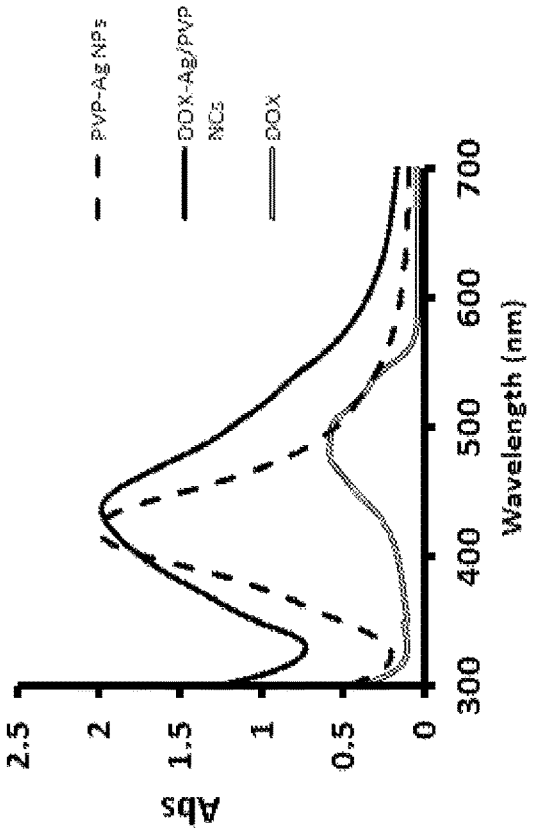
Figure 5D:
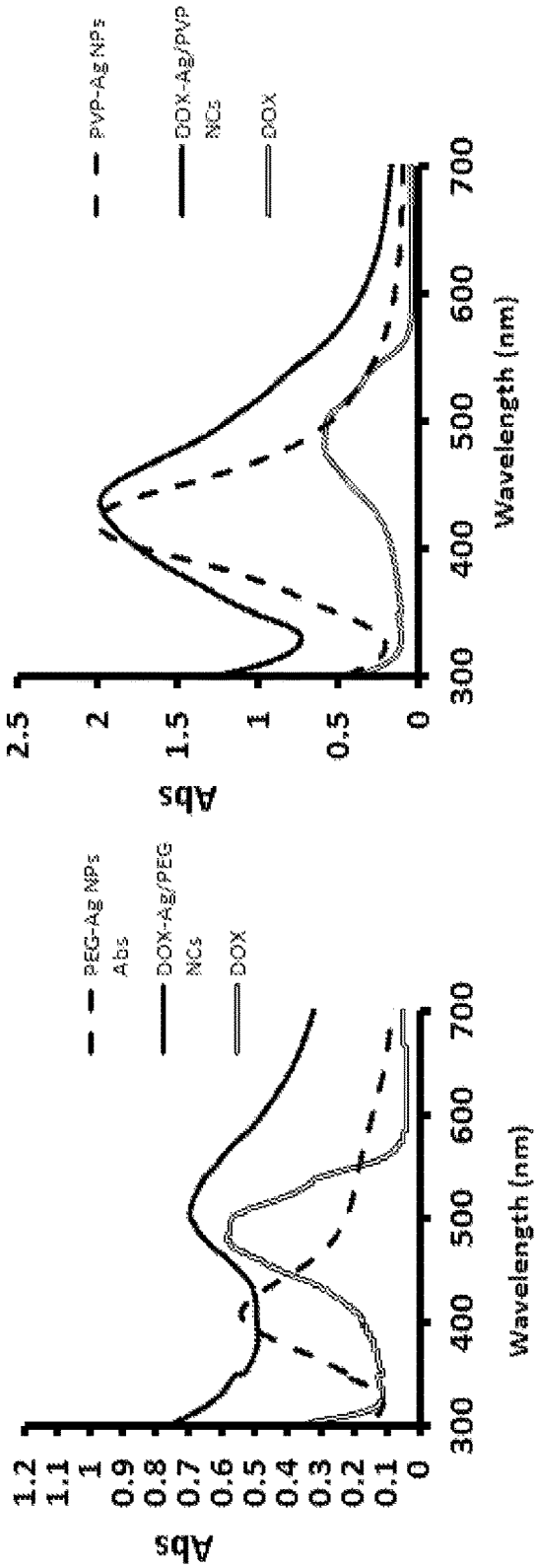

The NPs-based combinatorial therapy according to an embodiment of the present invention (FIG. 1) can be been prepared as follows:

(1) Preparation of silver nanoparticles coated with FDA-approved synthetic polymers (PVA, PEG and PVP), (2) Drug loading (DOX), and (3) In-vitro testing of free DOX alone, an individual type of Ag/polymeric (PVA, PEG and PVP) NPs alone, and DOX-Ag/polymeric (PVA, PEG and PVP) nanocarriers (NCs) on breast cancer cell line (MCF-7) and the cell viability and 50% inhibition concentration (IC50) were measured after 48 hrs incubation.

The in-vitro test was conducted using the MTT assay on breast cancer cell line (MCF-7) and human fibroblast cell line (1BR hTERT), which was performed as follows:

(1) Testing the cytotoxic effect of different concentrations (2, 4, 8, 10, and 12 µg/ml) of free DOX alone, (2) Testing the cytotoxic effect of AgNPs and core-shell Ag/polymeric (PVA, PEG, and PVP) NPs using different concentrations (10, 20, 50, and 100 µg/ml), and (3) Testing the cytotoxic effect of NPs-based combinatorial therapy of an individual type of DOX-Ag/polymeric NCs including DOX-loaded Ag/PVA NCs, DOX-loaded Ag/PEG NCs, and DOX-loaded Ag/PVP NCs using different concentrations (0.1, 0.2, and 1 µg/ml DOX).

A Prior Art Example to Contrast the Embodiments of the Present Invention

Hekmat et al. in-vitro examined the combination effect of commercially available Ethylenglycole-stabilized AgNPs (purchased from Bio-cera CO, Ltd, south korea) and DOX on breast cancer cell line (MCF-7). The in-vitro MTT test was performed as follows:

(1) Testing the cytotoxic effect of different concentrations of AgNPs alone (1.7, 2.55, 5, 8.5, 11.9, and 20.4 µg/ml), (2) Testing the cytotoxic effect of different concentrations of free DOX (0.0725, 0.145, 0.232, 0.319, 0.58, and 0.725 µg/ml), and (3) Testing the cytotoxic effect of AgNPs in combination with DOX of the following concentrations (0.174 and 0.232 µg/ml for DOX) and (1.7 and 2.55 µg/ml for AgNPs) (this combination was done by conventional addition), and then the cell viability and IC$_{50}$ were measured following 48 hrs incubation [20].

In-vitro MTT Results

The Cytotoxic Effect of AgNPs

After 48 hrs incubation, the cell viability was measured and the results were plotted in graphs (FIGS. 2A-D). From these graphs, IC$_{50}$ were determined to be 48 µg/ml for AgNPs and >100 µg/ml for Ag/PVA NPs and Ag/PEG NPs, and 42 µg/ml for Ag/PVP NPs (TABLE 1). Basically, AgNPs possess an anticancer action owing to their potential to translocate at the mitochondria and nucleus where releasing Ag$^+$ ions. The released Ag$^+$ ions trigger the generation of ROS mediating oxidation stress. The oxidation stress causes a series of cellular events including reduced the levels of glutathione (GSH) and superoxide dismutase (SOD), and elevated lipid peroxidation, which eventually lead to DNA damage and cancer cell death [21].

The difference in in-vitro results among different uncoated and coated AgNPs is mainly ascribed to the effect of polymeric coating. It has been well documented that NPs' surface coating controls AgNPs' dissolution, which is directly correlated with their cytotoxicity [22-24]. Results revealed that Ag/PVP NPs exhibited the highest cytotoxicity ($IC_{50}$: 42 µg/ml) as compared to AgNPs ($IC_{50}$: 48 µg/ml), core-shell Ag/polymeric (PVA and PEG) NPs ($IC_{50}$: above 100 µg/ml). Dobias and Bernier-Latmani reported that core-shell Ag/PVP NPs exhibited higher cytotoxic effect than AgNPs because Ag/PVP NPs exhibit an order of magnitude higher dissolution as compared to AgNPs. Ag/PVP NPs exhibit a higher dissolution rate because PVP polymer is non-charged, therefore, the detached PVP chains could not reduce $Ag^+$ ions and thus resulted into higher cytotoxic effect. However, the slow dissolution of AgNPs was ascribed to the ability of the carboxylic group of citrate to bind to $Ag^+$ ions, hence reducing $Ag^+$ to $Ag^0$ and decreasing AgNPs cytotoxicity [21]. However, Ag/PVA, and Ag/PEG NPs showed a minimal cytotoxic effect when compared to AgNPs and Ag/PVP NPs, owing to their higher stability and slower dissolution rate. Luo et al. also revealed that core-shell Ag/PEG NPs and Ag/PVA NPs exhibit a very slow dissolution owing to the binding of detached negatively charged PEG and PVA polymer chains with released $Ag^-$ ions, forming stable Ag-ligand complexes resulting in $Ag^+$ ions retention and decrease in cytotoxicity [26]. By comparing these results with the in-vitro results of AgNPs obtained from Hekmat et al. study, it was found that $IC_{50}$ of AgNPs was 55 µM equal to 9.35 µg/ml (TABLE 1). These results revealed that the used AgNPs are unstable and exhibit faster dissolution rate as compared to the invented AgNPs; since 100 µg/ml of the invented Ag/polymeric (Ag/PVA and Ag/PEG) NPs did not reach the same cytotoxic effect reached by 9.35 µg/ml of the ready-made AgNPs.

TABLE 1

Comparison between IC50 of AgNPs in the prior art (Hekmat et al.) and the invented Ag/polymeric NPs on breast cancer cell lines (MCF-7).

| P.O.C | Prior Art Hekmat et al. | The invented Ag/polymeric NPs | | |
|---|---|---|---|---|
| | AgNPs | Ag/PVA NPs | Ag/PEG NPs | Ag/PVP NPs |
| $IC_{50}$ | 9.35 µg/ml | >100 µg/ml | >100 µg/ml | 48 µg/ml |

The Cytotoxic Effect of NPs-based Combination Therapy (According to this Invention) and Conventional Combination Therapy (Present in the Prior Art)

The cell viability was measured after 48 hrs incubation with free DOX alone and NPs-based combination therapy. The results obtained from MTT assay were plotted in graphs (FIGS. 3A-E), the $IC_{50}$ was found to be 3.7 µg/ml for free DOX alone, 1-11.23 µg/ml for DOX-AgNCs, 0.19-3.4 µg/ml for DOX-Ag/PVA NCs, 0.14-3 µg/ml for DOX-Ag/PEG NCs, and 0.1-3.5 µg/ml for DOX-Ag/PVP NCs. These results revealed that the $IC_{50}$ of DOX-Ag/polymeric (PVA, PEG and PVP) NCs was achieved at a much lower dose of DOX and Ag, as compared to DOX-AgNCs, thus indicating the superiority of DOX-Ag/polymeric (PVA, PEG and PVP) NCs. The results also revealed that DOX-Ag/polymeric (PVA, PEG and PVP) NCs showed $IC_{50}$ at 10-fold reduced doses compared to free DOX alone. In addition to the low concentration of DOX, the $IC_{50}$ was achieved at very low concentration of NPs of 3.5 µg/ml for Ag/PVP NPs, 3.4 µg/ml for Ag/PVA NPs, and 3 µg/ml for Ag/PEG NPs, respectively. Taken together, the in-vitro results revealed that DOX-Ag/polymeric (PVA, PEG and PVP) NCs achieved the same efficacy of DOX alone, but with 95% reduced dose of DOX. The achieved synergic anticancer effect of DOX-NCs could be ascribed to two reasons: (i) the combined effect occurred due to the combination of both the cytotoxic effect of AgNPs along with the therapeutic effect of DOX, and (ii) the enrichment in internalization of DOX-Ag/polymeric NCs via endocytosis allowing the release of DOX inside the cell as compared to the passive diffusion mechanism of free DOX into the cells. Venkatpurwar et al. reported a significant enhancement in cytotoxicity of DOX-AuNCs on human glioma cell line (LN-229) compared to free DOX, possibly through enhanced cellular internalization owing to AuNPs mediated endocytosis [27]. Chen et al. also reported the passive intracellular accumulation of methotrexate-AuNCs confirming AuNCs mediated endocytosis followed by methotrexate release inside cancer cells [28].

On the other hand, the in-vitro results obtained by Hekmat et al. showed that the $IC_{50}$ of conventional combination therapy between AgNPs and DOX was 15 µM AgNPs+0.4 µM DOX, which is equal to 0.23 µg/ml DOX+2.55 µg/ml AgNPs. By comparing $IC_{50}$ results of the invented NPs-based combination therapy and conventional combination therapy present in the prior art (Hekmat et al.), it was clearly observsed that results of NPs-based combinatorial therapy showed a synergic anticancer effect similar to the prior art, but at a much lower dose of DOX. As shown in TABLE 2, NPs-based combinatorial therapy achieved an $IC_{50}$ but with around 40% reduced dose of DOX compared to DOX-Ag combination present in the prior art. The main difference between the invented NPs-based combination therapy and the combination therapy present in the prior art, is the type of combination.

In embodiment of this invention, the combination was based on loading NPs with a chemotherapeutic agent, DOX, while the combination in the prior art is based on simply adding AgNPs followed by DOX (without loading). However, in this invention, DOX was is physcially loaded on AgNPs through van der Waal bond. The large surface area of AgNPs offers a large loading capacity for DOX, which in turn results in enhancing the cellular uptake of DOX resulting in the imporved therapeutic efficiency in comparison to the prior art.

One can conclude that NPs-based combinatorial therapy possesses a synergism at a much lower dose of DOX, owing to the advantages of nanotherapeutics that include: passive cancer targeting and enrichment of cellular internationalization of drug via endocytosis—in comparison to the passive diffusion of free drug and combination therapy in the prior art. In addition, the DOX-core-shell Ag/polymeric NCs showed low toxicity on normal human fibroblast (1BR hTERT) cells. Therefore, the DOX dose can be reduced using this platform and in turn reduces its dose-dependent toxicity and adverse side effects.

TABLE 2

IC50 of the NPs-based combination therapy according to the invention compared to the DOX-Ag combination in the prior art.

| P.O.C | Prior Art Hekmat et al. DOX + AgNPs | The NPs-based combination therapy according to the invention | | |
|---|---|---|---|---|
| | | DOX-Ag/ PVA NCs | DOX-Ag/ PEG NCs | DOX-Ag/ PVP NCs |
| IC50 | 0.23 µg/ml DOX + 2.55 µg/ml | 0.19 µg/ml DOX 3.4 µg/ml | 0.14 µg/ml DOX − 3 µg/ml | 0.1 µg/ml DOX 3.5 µg/ml |

TABLE 2-continued

IC50 of the NPs-based combination therapy according to the invention compared to the DOX-Ag combination in the prior art.

| P.O.C | Prior Art<br>Hekmat et al.<br>DOX + AgNPs | The NPs-based combination therapy<br>according to the invention | | |
|---|---|---|---|---|
| | | DOX-Ag/<br>PVA NCs | DOX-Ag/<br>PEG NCs | DOX-Ag/<br>PVP NCs |
| % of reduction in DOX dose | AgNPs | Ag/PVA<br>NCs<br>18% | Ag/PEG<br>NCs<br>40% | Ag/PVP<br>NCs<br>57% |

Additional Results

Synthesis and Characterization of AgNPs and Core-shell NPs

The size and morphology of the prepared AgNPs and core-shell Ag/polyeric NPs were characterized by SEM, Image J analysis software and UV-visible spectroscopy. SEM images showed that the prepared AgNPs and core-shell Ag/polymeric NPs were spherical, mono-dispersed and well-dispersed (FIG. 4A-G). The size distribution histogram obtained from the Image J analysis software, showed that the average sizes of AgNPs and core-shell Ag/polymeric (PVA, PEG, and. PVP) NPs were 7.3±1.8 nm, 6.1±2.8 mn, 8.4±5.4 tun and 13.3±7.1 nm (FIGS. 4B, 4D, 4F, and 4H), respectively. The UV-Vis spectra of AgNPs, Ag/PVA NPs and Ag/PEG NPs (FIGS. 4A-D) showed a sharp surface Plasmon resonance (SPR) peak at ~400 nm, which is the characteristic peak of spherical, mono-dispersed and well-dispersed AgNPs [29-30]. However, the UV-Vis spectrum of Ag/PVP NPs (FIG. 4D) showed a sharp peak at 420 nm. Previous studies demonstrated that spherical and mono-dispersed Ag/PVP NPs of size ranging between 10-20 nm display a SPR band at ~412-437 nm [31]. The FT-IR spectra also confirmed the formation of AgNPs and core-shell Ag/polymeric (PVA, PEG, and PVP) NPs [31-34]. See also FIGS. 10-13.

Synthesis and Characterization of DOX-NCs

Following synthesis of Ag/NPs and core-shell Ag/polymeric NPs, each individual type of NP was loaded with DOX. The drug loading efficiency was determined based on DOX content in the supernatant. The drug loading efficiency percentages were determined to be: 58.3%, 54.9%, 56.5% and 62.5% for: AgNPs, core-shell Ag/PVA NCs, core-shell Ag/PEG NCs and Ag/PVP NCs, respectively. The bond between DOX and NPs was detected using UV-Vis spectra (FIGS. 5A-D) and SEM (FIGS. 6A-H). The UV-Vis spectra (FIGS. 5A-D) indicated that binding of DOX to NPs resulted in a red shift of the SPR peak of loaded NPs from 400 to ~500 nm.

In-vitro Drug Release

Figure 7A:
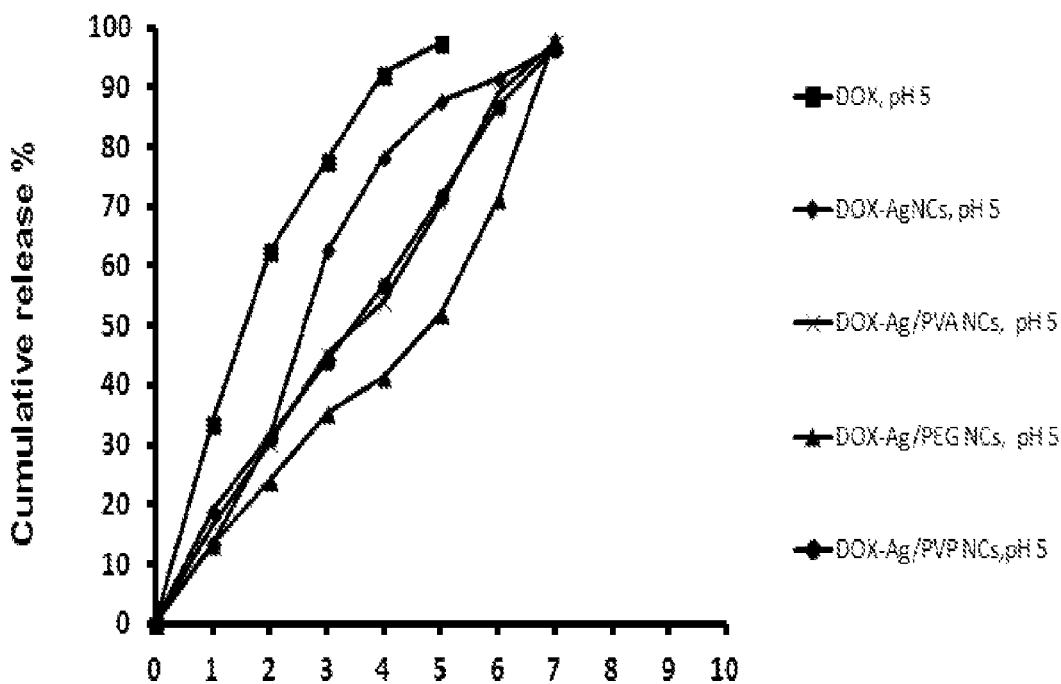
FIGS. 7A-B show according to an exemplary embodiment of the invention in-vitro release of free DOX, and DOX-NCs in Tris-HCl buffer pH 5 (FIG. 7A) and PBS pH 7.4 (FIG. 7B).
Figure 7B:
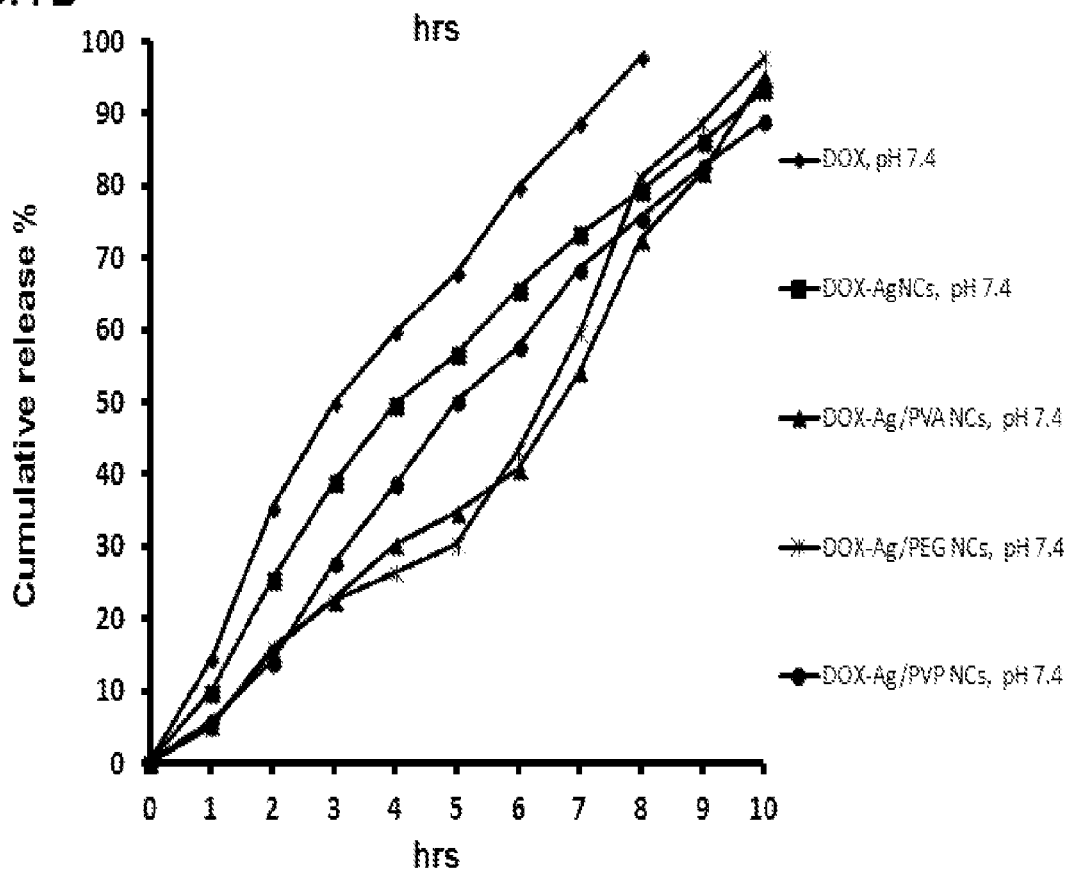
Figure 8B:
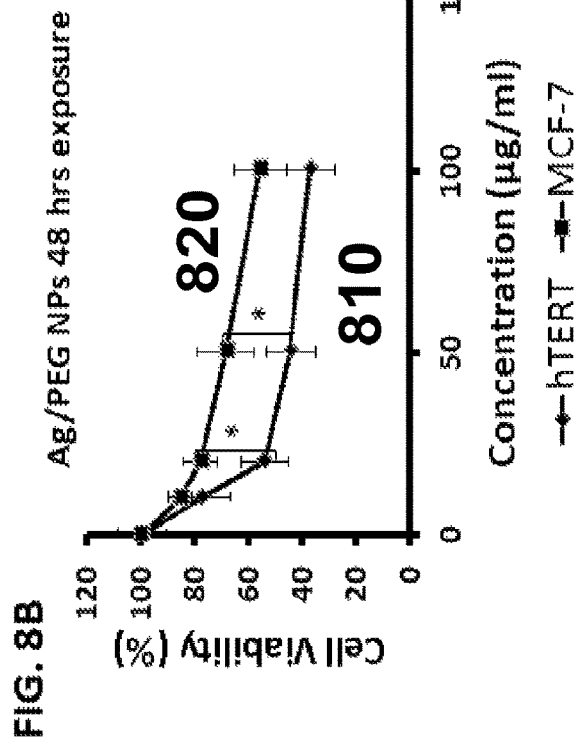
Figure 8D:
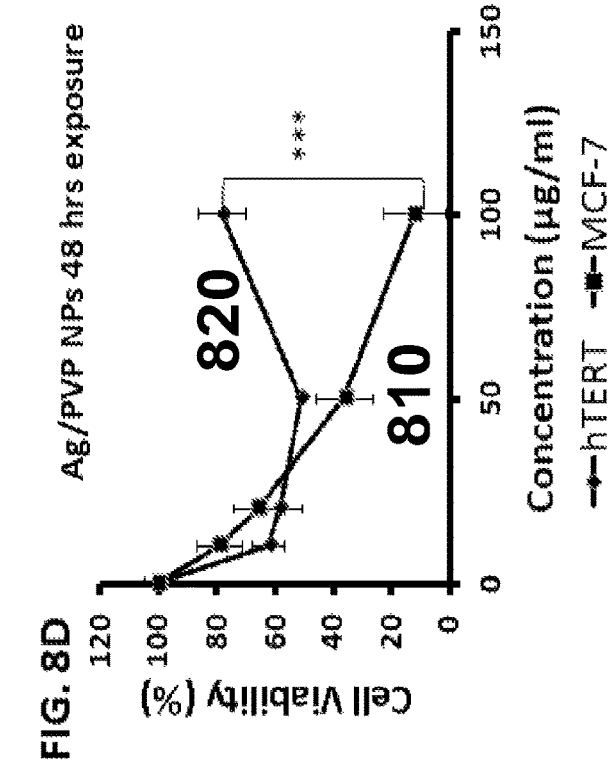
Figure 8A:
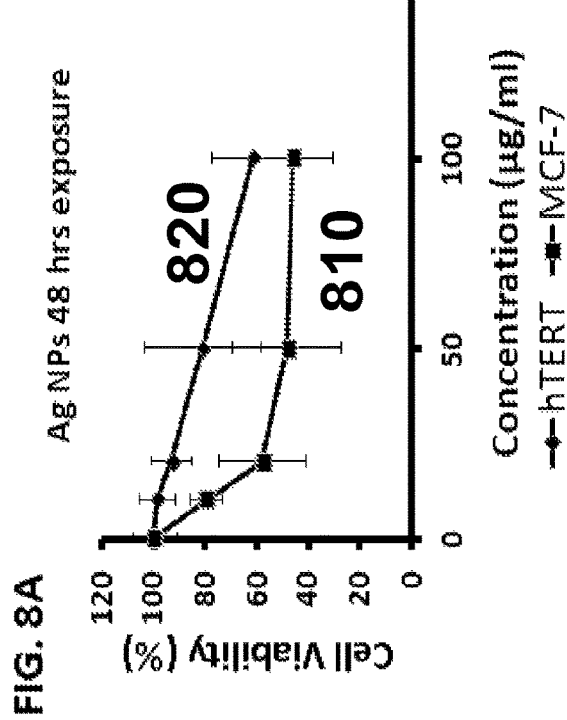
Figure 8C:
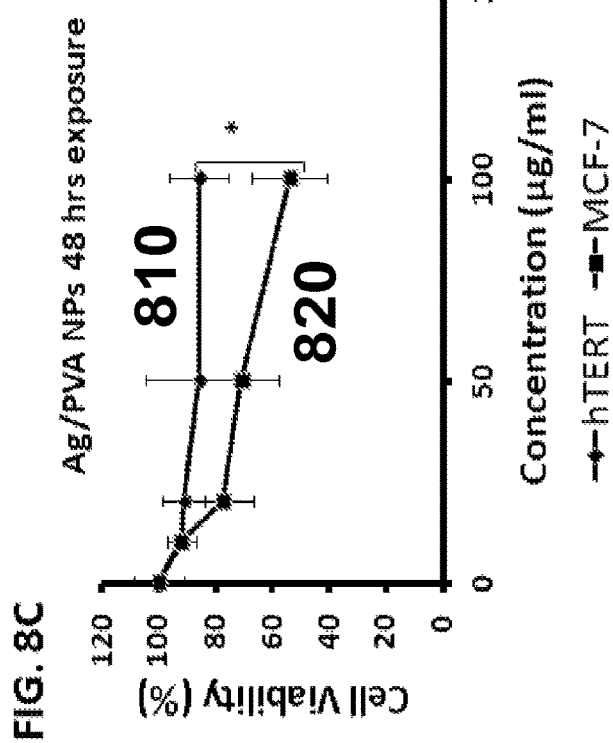
Figure 10:
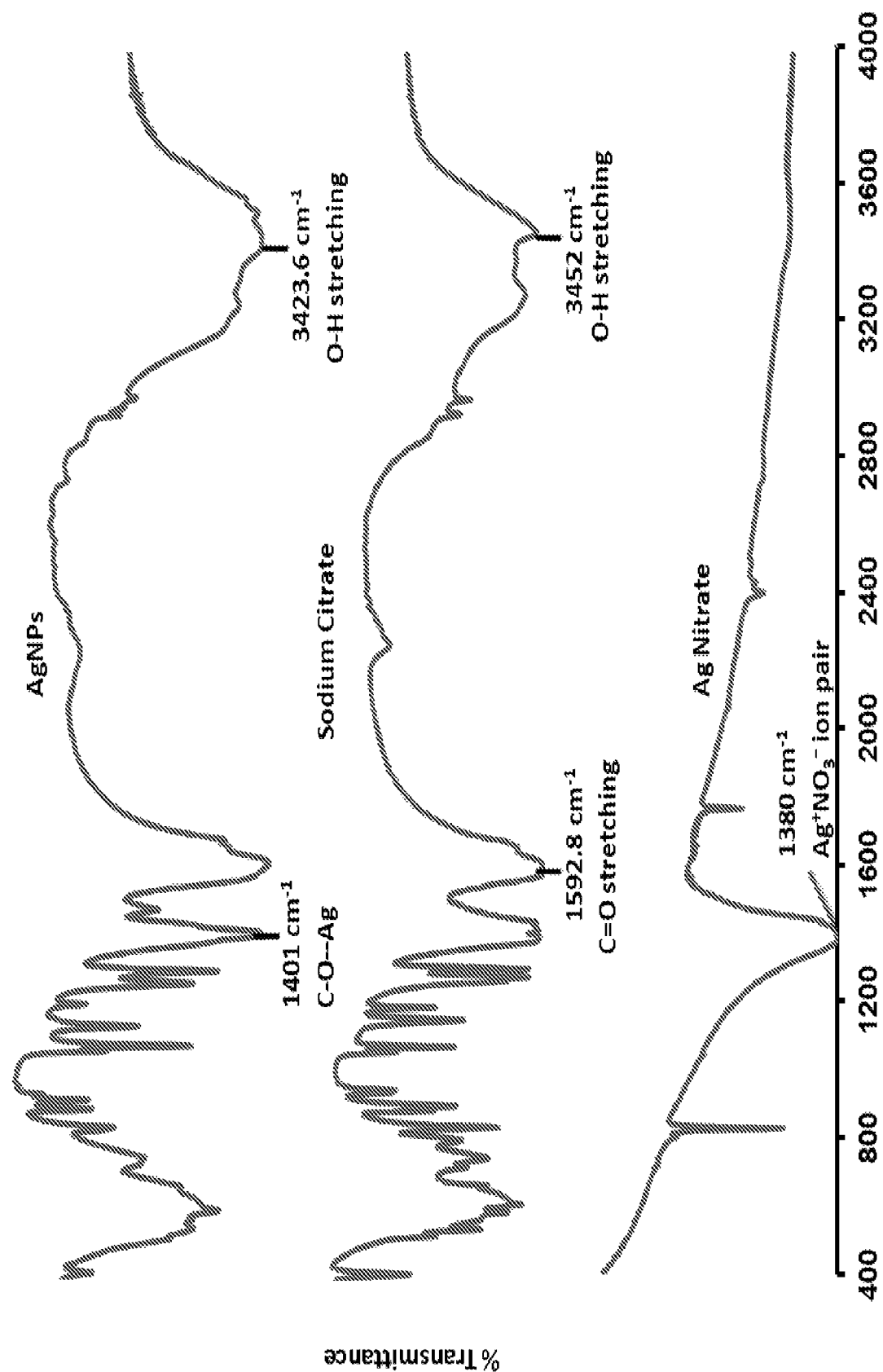
FIG. 10 shows according to an exemplary embodiment of the invention FTIR spectra of silver nitrate, sodium citrate, and AgNPs. The FT-IR spectra of AgNPs, trisodium citrate and $AgNO_3$ confirm the formation of AgNPs. By comparing the FT-IR spectra of AgNPs, sodium citrate and $AgNO_3$, the FT-IR spectra of AgNPs showed a band at 3423.6 $cm^{-1}$ that is not present in the FT-IR spectrum of $AgNO_3$. This band is attributed to O—H stretching between AgNPs and trisodium citrate. In addition, it was found that the band at 1592.8 $cm^{-1}$ is assigned for symmetric carboxylic group stretching mode of sodium citrate underwent a blue shift and appeared sharply at 1401 $cm^{-1}$ in the spectrum of AgNPs and thus confirming the stabilization of AgNPs by carboxylic group of trisodium citrate. Moreover, the spectrum of $AgNO_3$ displays a band at 1380 $cm^{-1}$ corresponding to ion pair $Ag^+NO_3^-$ that is not found in the spectrum of AgNPs due to the separation of $NO_3$ from its $Ag^1$ counterpart.
Figure 11:
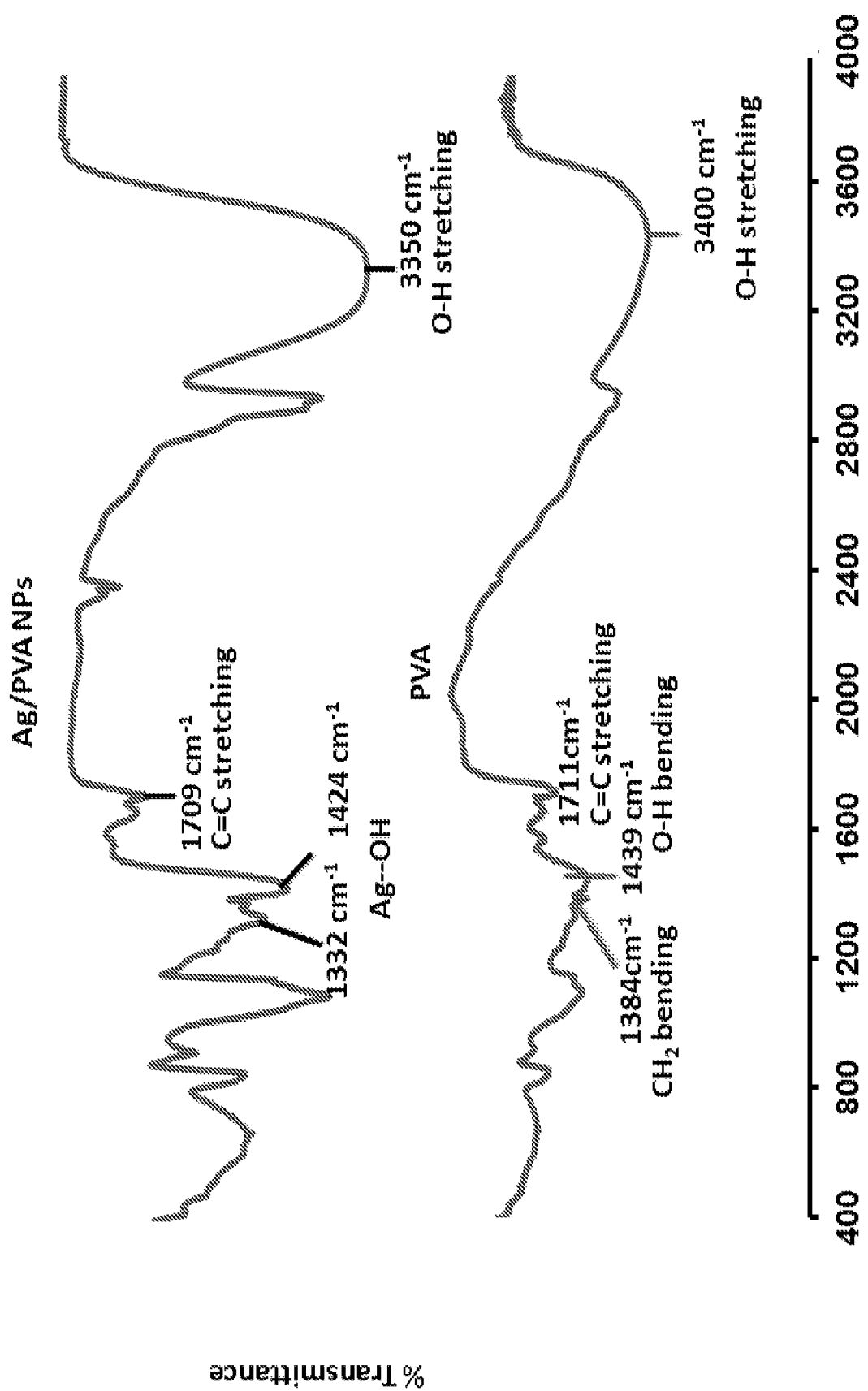
FIG. 11 shows according to an exemplary embodiment of the invention FTIR spectra of Pure PVA and core-shell Ag/PVA NPs. The FT-IR spectra of pure PVA and core-shell Ag/PVA NPs are found to be nearly similar. Both spectra show a broad band at 3400 $cm^{-1}$ for pure PVA and 3350 $cm^{-1}$ for core-shell Ag/PVA NPs respectively, which corresponds to the stretching vibration of hydroxyl group of PVA. Both FT-IR spectra show a band at 2942 $cm^{-1}$ is assigned to $CH_2$ asymmetric stretching vibration. The bands at 1711$cm^{-1}$ for pure PVA and 1709 $cm^{-1}$ for core-shell Ag/PVA NPs corresponds to C=C stretching mode. In addition, the band at 1655$cm^{-1}$ assigned to C=O group which could be contributed to the intra/inter molecular hydrogen bond with adjacent hydroxyl group. Moreover, both FT-IR spectra displayed a band at 1095 $cm^{-1}$ for pure PVA and 1093 $cm^{-1}$ for core-shell Ag/PVA NPs, which are assigned to C—O stretching of acetyl group on PVA back bone. Additionally, the band at 1439 $cm^{-1}$ and 1384$cm^{-1}$ for pure PVA may be attributed to $CH_2$ and O—H bending vibrations. However, these bands underwent a blue shift and appeared at 1424 $cm^{-1}$ and 1332 $cm^{-1}$ in the spectrum of core-shell Ag/PVA NPs. This blue shift of the bands observed at 1424 cm$^{-1}$ indicates that PVA polymer is adsorbed on the surface of AgNPs via the interaction of AgNPs and OH groups of PVA.
Figure 12:
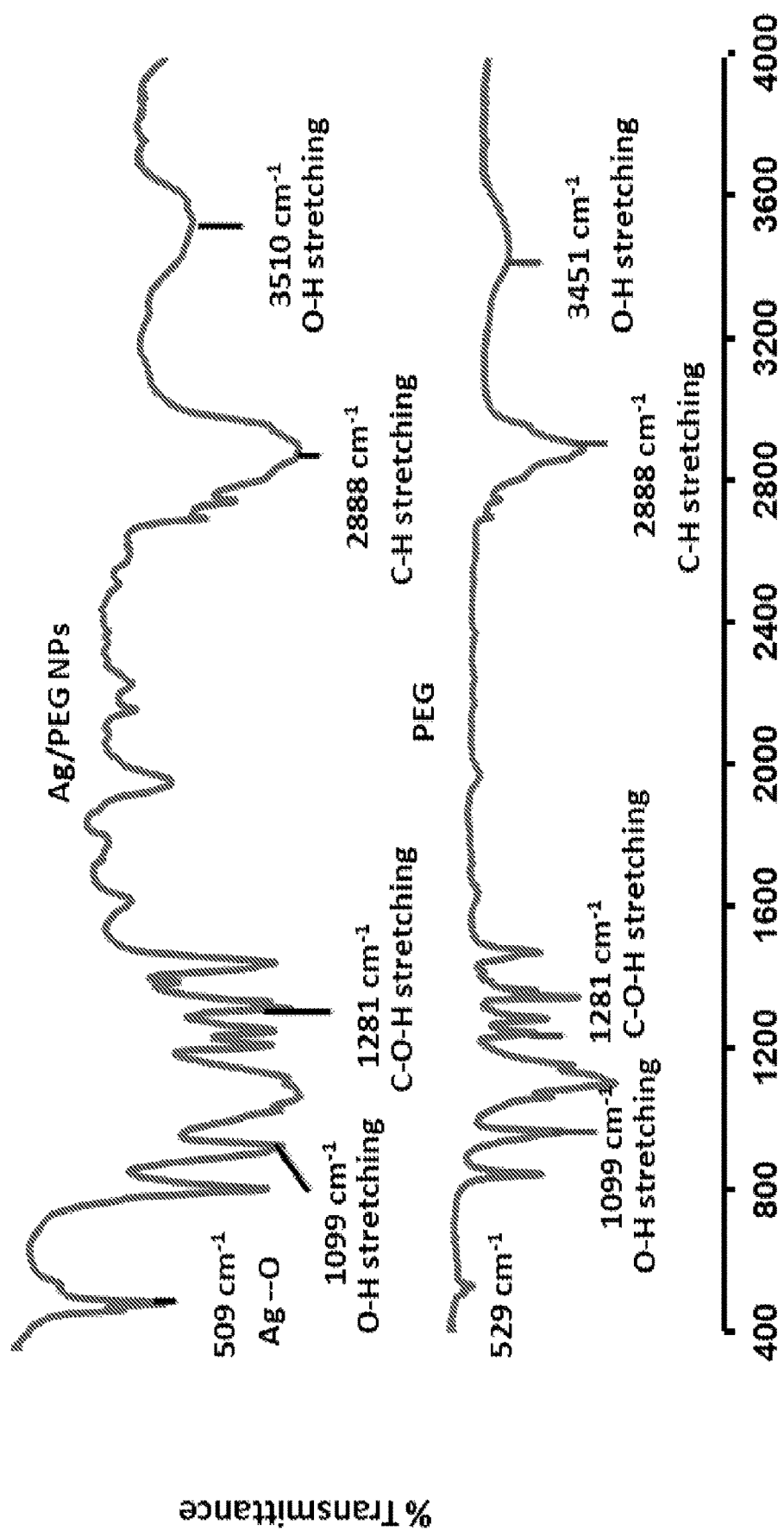
FIG. 12 shows according to an exemplary embodiment of the invention FTIR spectra of Pure PEG and core-shell Ag/PEG NPs. The FT-IR spectra of pure PEG and core-shell Ag/PEG NPs, also confirmed the formation of core-shell Ag/PEG NPs. The FT-IR spectra of pure PEG and core-shell Ag/PEG NPs are nearly identical. The FT-IR spectrum of pure PEG shows a band at 3451 cm$^{-1}$ corresponds to O—H stretching vibrations and a band at 2888 cm$^{-1}$ corresponds to C—H stretching vibrations. Both FT-IR spectra showed bands at 1466 and 1342 cm$^{-1}$, which are assigned to C—H bending vibrations. The stretching vibrations of alcoholic OH and C—O—H stretching are observed at 1281 and 1099 cm$^{-1}$ also appear in both spectra. However, the FT-IR spectrum of Ag/PEG NPs showed a broad band at 1099 cm$^{-1}$ as compared to FT-IR spectrum of PEG, which could be ascribed to C—O—H vibrations of AgNPs in PEG. Comparing the FT-IR of both pure PEG and the spectrum of core-shell Ag/PEG NPs, a strong band is observed at 509 cm$^{-1}$ at the spectrum of core-shell Ag/PEG NPs, which could be attributed to AgNPs banding with oxygen from hydroxyl groups of PEG chains and thus suggesting the existence of van der Waals interaction between the positively charged groups on the surface of Ag NPs and the negatively charged oxygen from the hydroxyl groups of PEG.
Figure 13:
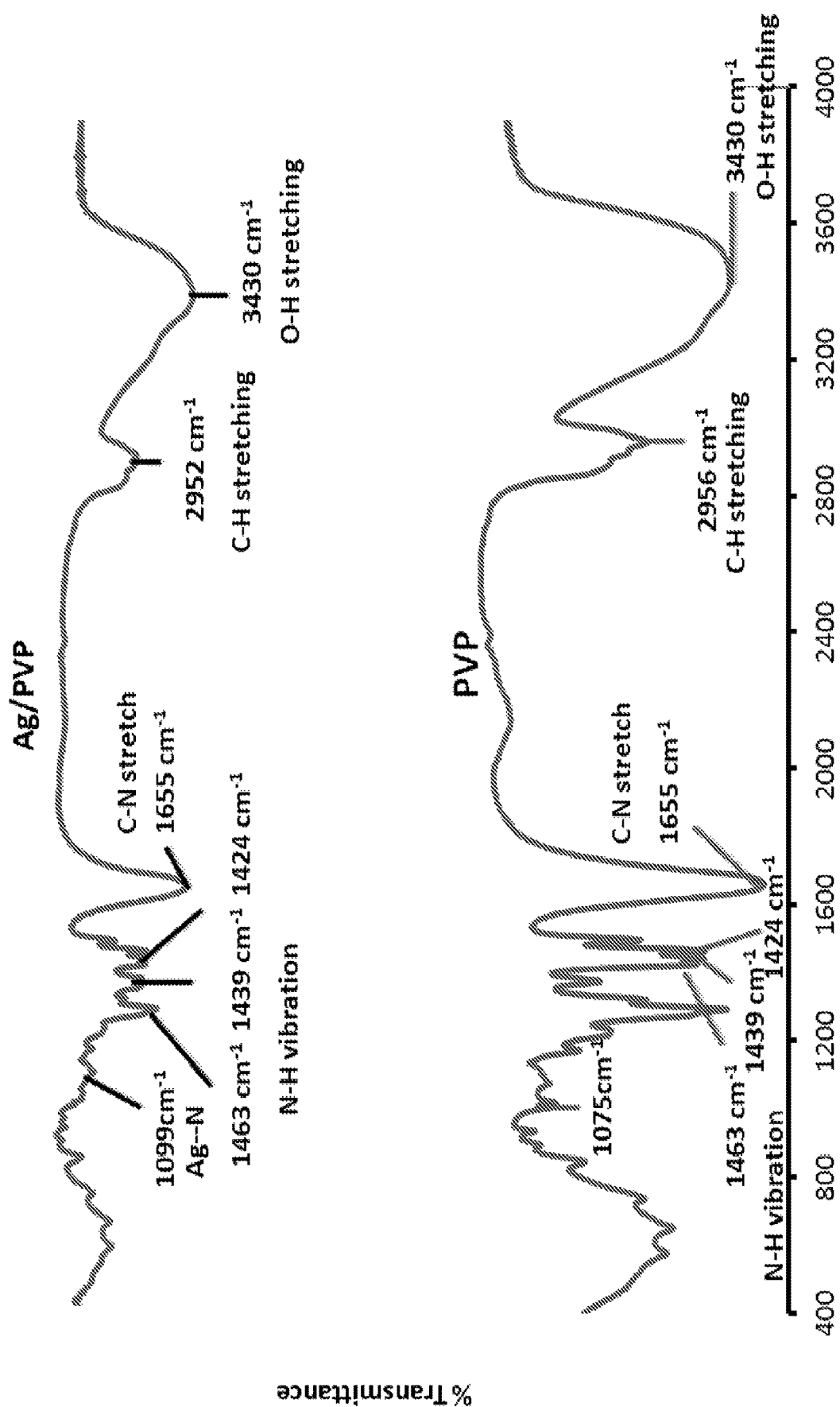
FIG. 13 shows according to an exemplary embodiment of the invention FTIR spectra of Pure PVP and core-shell Ag/PVP NPs. The FT-IR spectra of pure PVP and core-shell Ag/PVP NPs formed by polyol method shown are closely identical. Both spectra showed peaks at 3430 cm$^{-1}$ which corresponds to O—H stretching vibration of hydroxyl group and 2952 cm$^{-1}$ corresponding to symmetric stretching vibration of C—H bond. Both spectra also showed a sharp band at 1655 cm$^{-1}$ that corresponds to amide carbonyl stretch absorption and peaks at 1463, 1439, 1424 cm$^{-1}$ are assigned to the vibration of tertiary nitrogen. However, the FT-IR spectrum of core-shell Ag/PVP NPs displays a red shift at band 1099 cm$^{-1}$, compared to the band at 1075 cm$^{-1}$ in the spectrum of pure PVP. The red shift of band at 1099 cm$^{-1}$ confirms the involvement of pyrrolidyl nitrogen electrons in the formation of core-shell Ag/PVP NPs. This emphasizes that PVP is adsorbed at the silver NPs surfaces through donating electrons from the N atom to the Ag or the coordination between N and Ag. Wang et al. revealed that core-shell Ag/PVP NPs with diameters smaller than 50 nm are protected by PVP via a coordination bond between N in PVP and Ag as shown in while NPs with diameters greater than 50 nm both N and O in PVP coordinated with Ag.

Since the release behavior of DOX-NCs at the desired site is of a great importance for formulating an ideal cancer-targeted drug delivery system, in-vitro release studies were performed at two different pH values were tested: pH 7.4, which mimics the pH of the blood stream and pH 5, which mimics the pH of the endosomes within cancer cells. In-vitro results (FIG. 6A-B) that DOX-AgNCs, DOX-Ag/PVA NCs, DOX-Ag/PEG NCs and DOX-Ag/PVP NCs released 96.6%, 97.4%, 98% and 96.4% of DOX at pH 5. While at pH 7.4, the release percentages of DOX were 73.4%, 54.3%, 59.8% and 68.5% over the course of 6 hrs. On the other hand, free DOX solution was also used as a control and it was found that free DOX released 97.4% of DOX at pH 5, and 67.7% at pH 7.4 over 4 hrs. In-vitro release is shown of free DOX, and DOX-NCs in Tris-HCl buffer pH 5 (FIG. 7A) and PBS pH 7.4 (FIG. 7B).

In-vitro Cytotoxicity Assay

Effect of AgNPs and Core-shell Ag/polymeric on MCF-7 Cells and 1BR hTERT Cells

To assess the cytotoxic effect of AgNPs and core-shell Ag/polymeric NPs, MCF-7 and 1BR hTERT cells were exposed separately to different concentrations of NPs for 48 hrs. AgNPs and core-shell Ag/polymeric (PVA, PEG and PVP) NPs decreased the cell viability of MCF-7 cells and 1BR hTERT cells (FIGS. 8A-D) in a dose-dependent manner. The inhibitory concentration ($IC_{50}$) was estimated to be 48 µg/mL for AgNPs, 42 µg/mL for Ag/PVP NPs and greater than 100 µg/mL for both Ag/PVA NPs and Ag/PEG NPs on MCF-7 cells. The $IC_{50}$ of NPs in 1BR hTERT cells was 100 µg/mL for Ag NPs, Ag/PVA NPs, and Ag/PEG NPs, and 50 µg/mL for Ag/PVP NPs. The Ag/PVA and Ag/PVP NPs were more cytotoxic on cancer cells at the high concentration of 100 µg/mL, with Ag/PVP NPs being more cytotoxic on MCF-7 cancer cells (FIGS. 8A-D).

Effect of DOX-core-shell Ag/Polymeric NPs on MCF-7 Cells and 1BR hTERT Cells

To investigate the cytotoxic effect of NPs-based combinatorial therapy, first, different concentrations of free DOX (2, 4, 8, 10, and 12 µg/mL) were tested on MCF-7 and 1BR hTERT cells, and cell viability was determined after 48 hrs. $IC_{50}$ of free DOX on MCF-7 cells was determined to be 3.7 µg/mL (FIG. 14). Based on the $IC_{50}$ of free DOX, lower DOX-NCs concentrations than the calculated $IC_{50}$ of free DOX were selected (0.1, 0.2, and 1 µg/mL DOX) in order to assess whether the combination between DOX and NPs will induce synergism or not. The estimated $IC_{so}$ values of DOX-AgNCs, DOX-Ag/PVA NCs, DOX-Ag/PEG NCs and DOX-Ag/PVP NCs on MCF-7 cells were 1.00-11.23 µg/mL, 0.19-3.40 µg/mL, 0.14-3.00 µg/mL, and 0.10-3.50 µg/mL, respectively (FIGS. 9A-D). On the other hand, the estimated $IC_{so}$ values of DOX-NCs on 1BR hTERT cells were 1.00-11.23 µg/mL for DOX-AgNCs, NCs, DOX-Ag/PEG NCs, and DOX-Ag/PVP NCs, while it was estimated to be 0.60-9.00 µg/mL for DOX-Ag/PVA NCs (FIGS. 9A-D). All DOX-loaded core-shell Ag/polymeric NCs were more cytotoxic on cancer cells than normal cells. Notably, Dox-Ag/PVP combination was more cytotoxic than all three and was more cytotoxic on cancer cells.

CONCLUSION

In conclusion, mono-dispersed spherical AgNPs and core-shell Ag/polymeric (PVA, PEG, and PVP) NPs were successfully synthesized, loaded with DOX and in-vitro drug release of each individual type of DOX-NCs was investigated. Moreover, individual unloaded-NPs, free DOX and DOX-NCs were tested for in-vitro cytotoxicity on MCF-7 cells and 1BR hTERT cells. In-vitro MTT experiments demonstrated that core-shell DOX-Ag/polymeric NCs at much lower doses showed a synergic cytotoxic effect towards MCF-7 cells, and a lower cytotoxic effect on normal 1BR hTERT cells.

REFERENCES

1. Grayson, M. and Breast cancer. Nature 2012: p. 49-58.
2. Ferlay, J., I. Soerjomataram, and M. Ervik, GLOBO-CAN 2012 v1. 0, Cancer Incidence and Mortality Worldwide: IARC Cancer Base No. 10 [Internet], International Agency for Research on Cancer, 2013. 2012.
3. Siegel, R., D. Naishadham, and A. Jemal, Cancer statistics, 2013. CA: a cancer journal for clinicians, 2013. 63(1): p. 11-30.
4. Ismail, G. M., A. A. A. El Hamid, and A. G. A. ElNaby, Assessment of Factors that Hinder Early Detection of Breast Cancer among Females at Cairo University Hospital. World Applied Sciences Journal, 2013. 21(1).
5. Coley, H. M., Mechanisms and strategies to overcome chemotherapy resistance in metastatic breast cancer. Cancer treatment reviews, 2008. 34(4): p. 378-390.
6. Hortobagyi, G., Anthracyclines in the treatment of cancer. Drugs, 1997. 54(4): p. 1-7.
7. Thorn, C. F., et al., Doxorubicin pathways: pharmacodynamics and adverse effects. Pharmacogenetics and genomics, 2011. 21(7): p. 440.
8. Torti, F. M., et al., Reduced Cardiotoxicity of Doxorubicin Delivered on a Weekly ScheduleAssessment by Endomyocardial Biopsy. Annals of internal medicine, 1983. 99(6): p. 745-749.
9. Kaye, S. and S. Merry, Tumour cell resistance to anthracyclines—a review. Cancer chemotherapy and pharmacology, 1985. 14(2): p. 96-103.
10. Gianni, L., E. Salvatorelli, and G. Minotti, Anthracycline cardiotoxicity in breast cancer patients: synergism with trastuzumab and taxanes. Cardiovascular toxicology, 2007. 7(2): p. 67-71.
11. van Vlerken, L. E. and M. M. Amiji, Multi-functional polymeric nanoparticles for tumour-targeted drug delivery. 2006.
12. Chidambaram, M., R. Manavalan, and K. Kathiresan, Nanotherapeutics to overcome conventional cancer chemotherapy limitations. Journal of Pharmacy & Pharmaceutical Sciences, 2011. 14(1): p. 67-77.
13. Chouhan, R. and A. Bajpai, Real time in vitro studies of doxorubicin release from PHEMA nanoparticles. Journal of nanobiotechnology, 2009. 7(1): p. 5.
14. Aryal, S., C.-M. J. Hu, and L. Zhang, Polymeric nanoparticles with precise ratiometric control over drug loading for combination therapy. Molecular pharmaceutics, 2011. 8(4): p. 1401-1407.
15. A K, M., Preparation and Characterization of Folate Conjugated Nanoparticles of Doxorubicin using PLGA-PEG-FOL Polymer. Medicinal chemistry, 2012.
16. Hu, C.-M. J. and L. Zhang, Therapeutic nanoparticles to combat cancer drug resistance. Current drug metabolism, 2009. 10(8): p. 836-841.
17. Gabizon, A., H. Shmeeda, and Y. Barenholz, Pharmacokinetics of pegylated liposomal doxorubicin. Clinical pharmacokinetics, 2003. 42(5): p. 419-436.
18. Tanaka, T., et al., Nanotechnology for breast cancer therapy. Biomedical Microdevices, 2009. 11(1): p. 49-63.
19. Park, J., et al., Tumor targeting using anti-her2 immunoliposomes. Journal of Controlled Release, 2001. 74(1): p. 95-113.
20. Hekmat A, Saboury A A, Divsalar A., The effects of silver nanoparticles and doxorubicin combination on DNA structure and its antiproliferative effect against T47D and MCF7 cell lines. J Biomed Nanotechnology, 2012. 8(6):968-82.
21. Huynh, K. A. and K. L. Chen, Aggregation kinetics of citrate and polyvinylpyrrolidone coated silver nanoparticles in monovalent and divalent electrolyte solutions. Environmental science & technology, 2011. 45(13): p. 5564-5571.
22. Aswathy Ravindran, V. M., N. Chandrasekaran, Amitava Mukherjee, Selective colorimetric sensing of cysteine in aqueous solutions using silver nanoparticles in the presence of Cr3+. Talanta, 2011: p. 533-540.
23. Caballero-Diaz, E., et al., The Toxicity of Silver Nanoparticles Depends on Their Uptake by Cells and Thus on Their Surface Chemistry. Particle & Particle Systems Characterization, 2013. 30(12): p. 1079-1085.
24. Prathna, T., N. Chandrasekaran, and A. Mukherjee, Studies on aggregation behaviour of silver nanoparticles in aqueous matrices: effect of surface functionalization and matrix composition. Colloids and Surfaces A: Physicochemical and Engineering Aspects, 2011. 390(1): p. 216-224.
25. Dobias, J. and R. Bernier-Latmani, Silver release from silver nanoparticles in natural waters. Environmental science & technology, 2013. 47(9): p. 4140-4146.
26. Luo, C., et al., The role of poly (ethylene glycol) in the formation of silver nanoparticles. Journal of colloid and interface science, 2005. 288(2): p. 444-448.
27. Venkatpurwar, V., A. Shiras, and V. Pokharkar, Porphyran capped gold nanoparticles as a novel carrier for delivery of anticancer drug: In vitro cytotoxicity study. International journal of pharmaceutics, 2011. 409(1): p. 314-320.
28. Chen, Y.-H., et al., Methotrexate conjugated to gold nanoparticles inhibits tumor growth in a syngeneic lung tumor model. Molecular pharmaceutics, 2007. 4(5): p. 713-722.
29. Song W. et al. Preparation and storage of silver nanoparticles in aqeons polymers. Chinese Journal of Chemistry 27, 717-721 (2009).
30. Li L. et al. Controllable synthesis of monodispersed silver nanoparticles as standards for quantitative assessment of their cytotoxicity. Biomaterials 33, 1714-1721 (2012).
31. Augustine R, Rajarathinam K. Synthesis and Characterization of silver nanopartices and its immobilization on alginate coated sultures for the prevention of surgical wound infections and in-vitro release studies. International Journal of Nano Dimension, 205-212 (2012).
32. Khanna P. et al. Synthesis and characterization of Ag/PVA nanocomposite by chemical reduction method. Materials Chemistry and Physics 93, 117-121 (2005).
33. Malina D. et al. Silver Nanoparticles Synthesis with Different Concentrations of Polyvinylpyrrolidone. Digest. Journal of Nanomaterials & Biostructures (DJNB) 1527-1534 (2012).
34. Wang H. et al. Mechanisms of PVP in the preparation of silver nanoparticles. Materials Chemistry and Physics 94, 449-453 (2005).

What is claimed is:
1. A nano-particle based composition for a combinational therapy for treatment of breast cancer comprising: doxorubicin physically loaded on core-shell silver polymeric nanoparticles with a ratio of 3.3-5.5 parts doxorubicin to 1 part silver to 2-10 parts polymer,
wherein the core-shell silver polymeric nanoparticles comprises the silver in the core and the shell comprises the polymer,
wherein the polymer is poly-vinyl alcohol (PVA), poly-ethylene glycol (PEG), or poly-vinyl pyrrolidone (PVP),
wherein the doxorubicin is present in the silver core,
wherein the silver core is stabilized by sodium citrate, wherein the concentration of the doxorubicin in the composition is less or equal to 0.2 µg/ml, and wherein the core-shell silver polymeric nanoparticles act as nanocarriers and anti-cancer agents for the treatment of breast cancer.

2. The composition as set forth in claim 1, wherein each core-shell silver polymeric nanoparticle has a width of 5 nm to 20 nm.

3. The composition as set forth in claim 1, wherein each core-shell silver polymeric nanoparticle has a width of 20 nm to 40 nm.

* * * * *